US011974848B2

United States Patent
Angle et al.

(10) Patent No.: US 11,974,848 B2
(45) Date of Patent: May 7, 2024

(54) LOW-AREA, LOW-POWER NEURAL RECORDING CIRCUIT, AND METHOD OF TRAINING THE SAME

(71) Applicants: Paradromics, Inc., Austin, TX (US); Caeleste CVBA, Mechelen (BE)

(72) Inventors: Matthew R. Angle, Austin, TX (US); Robert Edgington, Campbell, CA (US); Aamir Ahmed Khan, Morgan Hill, CA (US); Bart Dierickx, Edegem (BE); Peng Gao, Korbeek-Lo (BE); Amir Babaiefishani, Ghent (BE); Ahmed Abdelmoneem, Leuven (BE); Bert Luyssaert, Ghent (BE); Jean Pierre Vermeiren, Haacht (BE)

(73) Assignees: CAELESTE CVBA, Mechelen (BE); PARADROMICS, INC., Austin, TX (US)

( * ) Notice: Subject to any disclaimer, the term of this patent is extended or adjusted under 35 U.S.C. 154(b) by 994 days.

(21) Appl. No.: 16/591,568

(22) Filed: Oct. 2, 2019

(65) Prior Publication Data

US 2020/0046240 A1 Feb. 13, 2020

Related U.S. Application Data

(63) Continuation of application No. PCT/US2018/027669, filed on Apr. 13, 2018.
(Continued)

(51) Int. Cl.
*A61B 5/05* (2021.01)
*A61B 5/00* (2006.01)
(Continued)

(52) U.S. Cl.
CPC .............. *A61B 5/24* (2021.01); *A61B 5/291* (2021.01); *A61B 5/7225* (2013.01); *A61B 5/725* (2013.01);
(Continued)

(58) Field of Classification Search
CPC .............. A61B 5/24; A61B 5/30; A61B 5/316
See application file for complete search history.

(56) References Cited

U.S. PATENT DOCUMENTS

| 3,810,067 A | 5/1974 | Heidecker |
| 5,268,684 A | 12/1993 | Allen et al. |

(Continued)

FOREIGN PATENT DOCUMENTS

| CA | 2209524 C | * 11/2006 | ........... H04B 1/7085 |
| WO | WO-2005027720 A2 | * 3/2005 | ........... A61B 5/0205 |
| WO | WO-2018191725 A1 | 10/2018 | |

OTHER PUBLICATIONS

EP18784010.3 Extended European Search Report dated Dec. 23, 2020.
(Continued)

*Primary Examiner* — Michael J D'Abreu
(74) *Attorney, Agent, or Firm* — Wilson Sonsini Goodrich & Rosati

(57) ABSTRACT

A sensor circuit that is capable of sensing of neural action potentials is disclosed. The circuit can be designed to minimize power dissipation and total silicon area so that it can be incorporated into a massively parallel sensor array and ultimately implanted in the body (e.g. into the brain) in a safe manner. The circuit can also be designed to be tunable such that it can be optimized in silico prior to fabrication, and can be optimized through the use of controllable current sources after fabrication.

24 Claims, 13 Drawing Sheets

Related U.S. Application Data

(60) Provisional application No. 62/485,857, filed on Apr. 14, 2017.

(51) Int. Cl.
*A61B 5/24* (2021.01)
*A61B 5/291* (2021.01)

(52) U.S. Cl.
CPC ............ *A61B 5/726* (2013.01); *A61B 5/7282* (2013.01); *A61B 5/6814* (2013.01); *A61B 5/7203* (2013.01); *A61B 5/7285* (2013.01); *A61B 2562/046* (2013.01); *H03F 2200/165* (2013.01)

(56) References Cited

U.S. PATENT DOCUMENTS

| | | |
|---|---|---|
| 6,349,222 B1 | 2/2002 | Hafiz |
| 2001/0038312 A1 | 11/2001 | Smith et al. |
| 2001/0056450 A1 | 12/2001 | Kiriaki |
| 2003/0191408 A1 | 10/2003 | Montgomery, Jr. |
| 2005/0090756 A1 | 4/2005 | Wolf et al. |
| 2005/0121598 A1 | 6/2005 | Nygard |
| 2005/0180763 A1 | 8/2005 | Jurzitza |
| 2005/0212589 A1 | 9/2005 | Batruni |
| 2007/0167815 A1 | 7/2007 | Jacobsen et al. |
| 2008/0294579 A1 | 11/2008 | Rapoport et al. |
| 2009/0105587 A1 | 4/2009 | Petersen et al. |
| 2009/0224164 A1 | 9/2009 | Lewellen et al. |
| 2010/0176866 A1 | 7/2010 | Fey et al. |
| 2010/0231794 A1 | 9/2010 | Robertson et al. |
| 2011/0163166 A1 | 7/2011 | Wang et al. |
| 2013/0262352 A1 | 10/2013 | Sung et al. |
| 2014/0200681 A1 | 7/2014 | Kennedy et al. |
| 2015/0205267 A1 | 7/2015 | Hsieh et al. |
| 2016/0278713 A1 | 9/2016 | Shoaran et al. |

OTHER PUBLICATIONS

Rapoport, B. Neural prosthetics for paralysis : algorithms and low-power analog architectures for decoding neural signals, Thesis, Massachusetts Institute of Technology (Feb. 5, 2007). 122 pages.
PCT/US2018/027669 International Search Report and Written Opinion dated Jun. 26, 2018.

\* cited by examiner $V_{ip} = V_{fb}$
$V_{bp} = V_o - V_{fb}$
$V_{hp} = V_o(I_{max}) - V_{fb}$

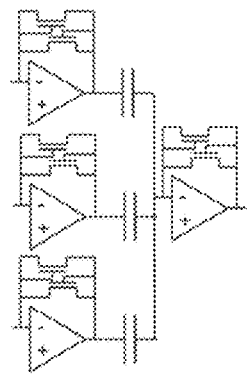 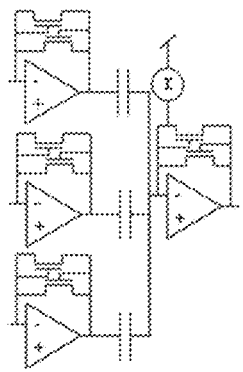 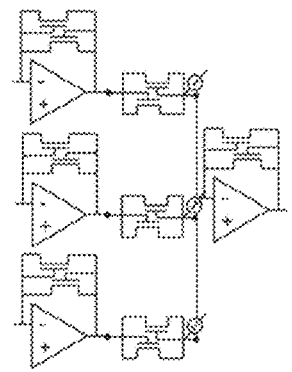 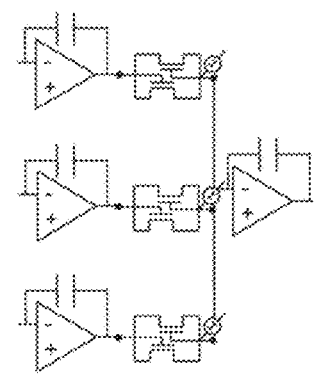
FIG. 9A    FIG. 9B    FIG. 9C    FIG. 9D
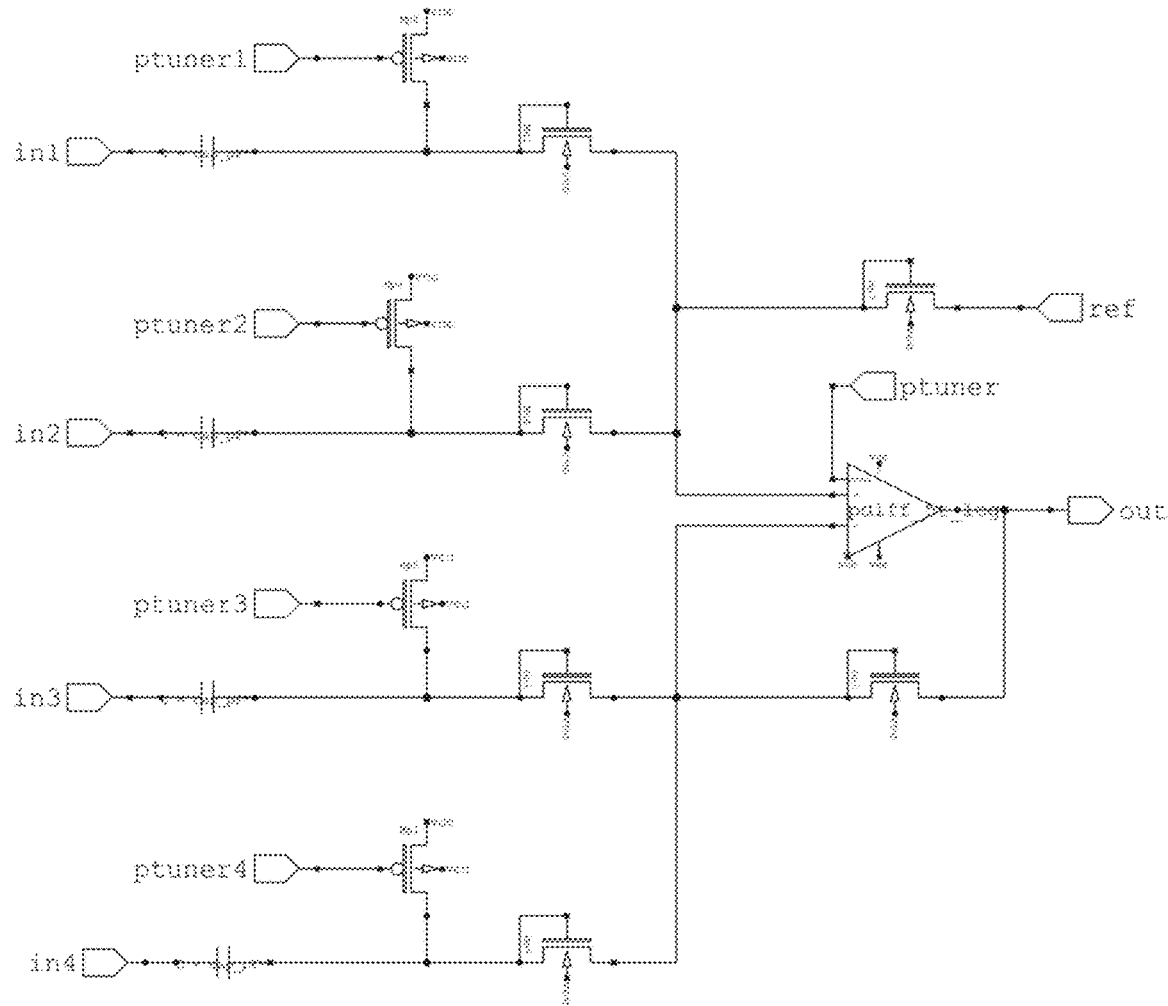
FIG. 10

LOW-AREA, LOW-POWER NEURAL RECORDING CIRCUIT, AND METHOD OF TRAINING THE SAME

CROSS-REFERENCE TO RELATED APPLICATION

This application is a continuation application of International Application No. PCT/US18/27669, filed on Apr. 13, 2018, which application claims the benefit of U.S. Provisional Patent Application No. 62/485,857, filed Apr. 14, 2017, which applications are incorporated herein by reference in their entirety.

BACKGROUND

Neural recording technology is of vital importance. It allows researchers to collect data about brain functionality to discover causes and cures for neurological diseases. It also enables neuroprosthetic technologies where brain activity can be used to control motor prostheses and other digital devices such as computers. In both cases, the utility of a neural recording device is greatly increased if it can record activity from many neurons individually and simultaneously. For this reason there is much interest in developing massively parallel neural recording devices, i.e. neural probes with many independent recording sites.

It is known in the field of neuroscience and neurotechnology that CMOS VLSI provides a powerful platform for creating massively parallel neural recording and stimulation electronics. These CMOS arrays can either be placed directly in contact with neurons or neural tissue, or they can be bonded to electrode arrays such as microwire bundles. It has also been observed that high density CMOS arrays present distinct challenges for implantation in the body. Namely, for implantation, the area and power requirements of such a device are severely constrained.

SUMMARY

The present disclosure addresses at least the above challenges, by providing one or more sensor circuit(s) that are designed to minimize power dissipation and total silicon area so that they can be incorporated in a massively parallel sensor array and implanted in the body (e.g. into the brain) in a safe manner. The sensor circuit(s) disclosed herein are also designed to be tunable in that they can be optimized in silico prior to fabrication, and can be optimized through the use of controllable current sources after fabrication. The sensor circuit(s) disclosed herein can be capable of compressive sensing of neural action potentials. High density neural recording probes can be used to gather electrical signals from the brain. Once recorded, these signals can be used to better understand the function of neural circuits, or the signals can be used to enable brain-control of computers and other prosthetic devices.

Embodiments of the present disclosure can include one or more of the following features or advantages: (1) The incoming action potential spike signals can be transformed using analog circuits to avoid the cost of digitizing the raw spike waveforms. (2) The transformed signal(s) can be digitized at a much lower bit rate than would otherwise have been required to transmit the same amount of pertinent information through digitization of the unprocessed raw signal (i.e. Nyquist sampling). (3) The analog circuits can be layered in the style of a fully or partially connected cascade feed-forward or recurrent neural networks. (4) The analog circuits can be configured to build up arbitrary transfer functions by combining simple filters and operators, either by placing the components in series or by summing the outputs of multiple filters (or chains of filters) using summing amplifiers or a combination of both. (5) The final analog output layer of the circuit can be made up of summing amplifiers. (6) The output of the summing amplifiers can be sampled and/or digitized by low power comparators and/or peak detectors and/or in-pixel ADC. (7) The analog circuits can use tunable transistors in place of resistors. (8) The analog circuit can minimize the total area dedicated to capacitors while still maintaining very low noise. (9) The circuit topology can allow for automated tuning of its components and interconnections to produce target outputs. (10) During in silico training, the circuit simulation can optionally be combined with an artificial neural network (ANN), and the stacked circuit and ANN can be trained simultaneously in order to find efficient encoding schemes at the output of the circuit. In this paradigm, the output layer of the circuit can act as the low-dimensional information bottleneck (as found in autoencoders) trained to perform dimensional reduction. The circuit(s) disclosed herein can therefore be highly amenable to being trained for compression, even when the optimal compression scheme was not known a priori.

According to an aspect of the disclosure, a neural data processor is provided. The neural data processor can comprise an analog circuit configured to process an input neural signal that is collected with aid of a sensing device. The analog circuit can comprise (1) at least two filters configured to transform the neural signal, and (2) at least one summing element configured to sum transformed outputs of the at least two filters, to process the neural signal and thereby extract a plurality of features from the neural signal.

In some embodiments, the sensing device may comprise at least one microelectrode, and the neural signal comprises an extracellular electrical recording collected using the at least one microelectrode. In some cases, the sensing device may comprise an optical sensor, and the neural signal may comprise a change in light intensity.

In some embodiments, the at least one summing element may comprise a plurality of summing elements. In some embodiments, (1) the filters can be configured having a set of predefined complex poles and zeros, and (2) the plurality of summing elements can be configured having a set of predefined summing weights, such that outputs of the plurality of summing elements convey temporal features of the neural signal. In some cases, the analog circuit can be configured to extract the plurality of features based on an a priori feature set derived from previously recorded and/or modeled neural activity. The a priori feature set can be encoded in the filters and the at least one summing element.

In some embodiments, the plurality of filters and the plurality of summing elements can be implemented as cascading layers in the analog circuit. In some instances, the plurality of summing elements may comprise linear summing circuits. Additionally or optionally, the plurality of summing elements may comprise nonlinear summing circuits. In some cases, the nonlinear summing circuits may comprise an artificial neuron.

In some embodiments, the plurality of filters and the plurality of summing elements can be collectively used to encode one or more linear transfer functions. Alternatively, the plurality of filters and the plurality of summing elements can be collectively used to encode one or more nonlinear transfer functions. The one or more transfer functions may approximate a correlation or convolution operation(s) of the neural signal with a linear basis set, and decomposition of the neural signal may be based on the linear basis set. In some cases, the basis set may be selected based on analysis of prior neural signal data. Alternatively, the basis set need not be selected based on an explicit statistical prior. In some embodiments, the basis set may be approximated by linear summations and/or cascades of one or more filter transfer functions. The linear summations and/or cascades of the one or more filter transfer functions may be implemented as active filter circuits and summing amplifiers. In some cases, the basis set may be chosen from an arbitrary set of basis functions including wavelets. In some embodiments, the output of one or more summing amplifiers can be further acted upon by additional filters and/or operators. In some embodiments, tunable transistors can be used in place of resistors within the analog circuit.

In some embodiments, the analog circuit may comprise a plurality of stages comprising of (1) a first stage, (2) a second stage, and (3) a third stage, wherein the filters are implemented in the second stage, and the summing elements are implemented in the third stage. In some cases, the first stage may comprise a low-noise amplifier and signal conditioning circuit configured to amplify and condition the neural signal before it is provided to the plurality of filters in the second stage. In some cases, the second stage may further comprise one or more nonlinear operators. The filters can be programmable for adaptation to a plurality of different types of feature extraction. The summing elements can be programmable to provide different types of summing behavior. The filters can be optimized for linear behavior, low power dissipation, and/or a reduced circuit area or footprint. In some embodiments, the predefined weights of the summing element can be optimized for linear behavior, dynamic range of weights, power dissipation, and/or a reduced circuit area or footprint.

In some embodiments, the analog circuit can be configured to provide one or more outputs to an event detection and sampling circuit. In some cases, the event detection and sampling circuit can be provided on a same chip as the analog circuit. In some cases, the event detection and sampling circuit is not a peripheral device to the analog circuit. In some cases, the processor may further comprise the event detection and sampling circuit. The processor can be implemented within a pixel on the chip. In some embodiments, an array of sensors may be provided on the chip. The array may comprise a plurality of the pixels and the processors. In some cases, the pixel density in the array can be ≥2,500 pixels/cm$^2$. In some cases, the pixel density in the array can be ≥15,000 pixels/cm$^2$. In some embodiments, the array of sensors may comprise an array of CMOS sensors. In some embodiments, the pixels or a subset of pixels in the array may comprise circuitry to extract local field potentials (LFPs) of the neural signal. In some embodiments, each sensor may be bonded to a passive electrode including an ECoG array, an array of microwires, an array of silicon probes, or an array of flexible electronic probes. In some cases, the array may be part of an active silicon probe that is inserted into brain. In some embodiments, each sensor can be in direct contact with neurons or neural tissue via metallization, organic semiconductors, III-V semiconductors, IV semiconductors, or through a capacitive passivation film. In some embodiments, the analog circuit described above is also capable of processing non-neural transient signals including optical, seismic, radar, or ultrasound.

In some embodiments, the outputs of the analog circuit may collectively constitute a low rank approximation of a neural signaling event when sampled at a specific point in time during or after the neural signaling event. The event detection and sampling circuit can be configured to transmit values of all of the outputs from the analog circuit when one or more triggering conditions are met.

In some embodiments, the event detection and sampling circuit can be configured to transmit the values at a time instance only when the one or more triggering conditions are met. In some cases, the event detection and sampling circuit does not transmit any values when the one or more triggering conditions are not met, so as to reduce an overall data transmission rate of the system.

In some embodiments, the one or more outputs from the analog circuit may comprise a master output and one or more slave outputs. The one or more triggering conditions may comprise a peak value of the master output exceeding a threshold. In some instances, the peak value of the master output may be transmitted and recorded only when the peak value exceeds the threshold. Instantaneous values of the one or more slave outputs can be synchronously transmitted and recorded at the moment the master output reaches a peak, whenever that peak value exceeds a threshold. In some embodiments, the threshold can be dynamically derived from the master output or the neural signal. In some cases, the dynamic threshold can be proportional to the root mean square value of the master output or the neural signal. In some cases, the threshold is a fixed value. In some cases, the threshold can be a value that is programmed externally and input to said processor. The event detection and sampling circuit can be configured to transmit the values from the analog circuit for digitization.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the various principles are utilized, and the accompanying drawings of which:

FIGS. 9A, 9B, 9C, and 9D illustrate summing amplifier topologies that can be implemented in the summation stage, in accordance with some embodiments;

FIG. 10 shows a summing amplifier with positive and negative input weights set by diode-connected transistors, in accordance with some embodiments;

DETAILED DESCRIPTION

I. Operation/Design Constraints

Thermal Constraints

Figure 1:
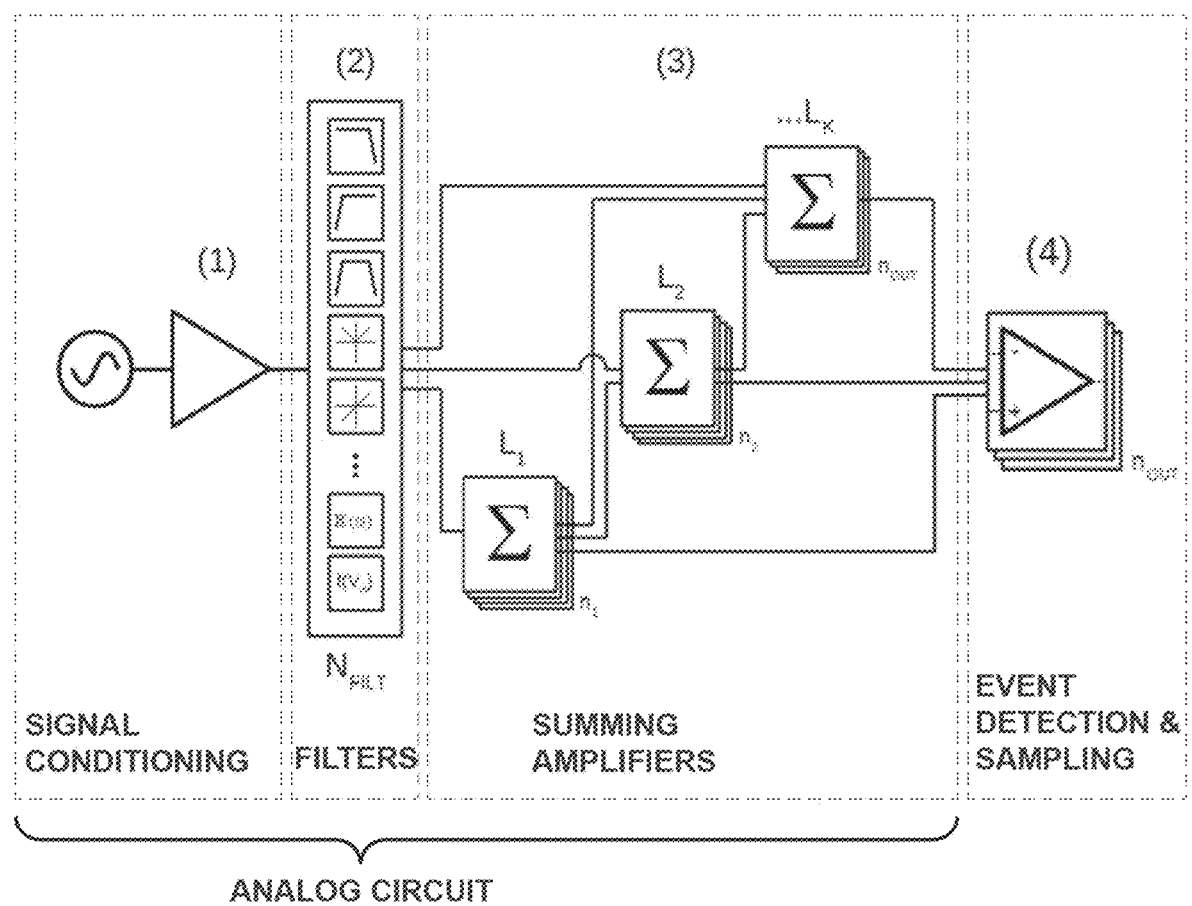
FIG. 1 illustrates a circuit architecture in accordance with some embodiments.

An important constraint for an implantable CMOS array is heat dissipation. An implant should not change the local temperature of surrounding brain tissue by more than 1-2° C. Practically, this means that an implant of dimensions, for example, ~1 cm×1 cm×1 mm should not dissipate more than 200 mW of power. For a 512×512 array, this would mean a per-pixel power rating of less than 0.76 µW, or for a 256×256 array, this would mean a per-pixel power rating of less than 3 µW.

To put this very low per-pixel power budget into context, it is useful to consider the energy required to digitize neural recording data for subsequent processing. Neural data is typically digitized at a rate of 20 kHz. Assuming a conversion energy of 100 fJ per conversion step, this leads to a digitization cost of 25 pJ per 8-bit sample or 400 pJ per 12-bit sample, i.e. 0.5 µW or 8 µW per pixel respectively at 20 kHz sampling rate.

As such, continual 20 kHz, 12-bit digitization in each pixel is unlikely to be acceptable from a power standpoint. At the same time, dramatically reducing either the bandwidth or bit depth of the signal would likely discard important information and compromise recording quality.

The conventional paradigm in neural signal acquisition and analysis is to: (1) amplify, (2) digitize, and then (3) process. When considering the power constraints for high density CMOS arrays, a need exists to utilize a different strategy to convey the same neural information. Preferably the information is at least partially processed prior to digitization, to avoid sampling at an unacceptable, "expensive" rate*depth (bit rate).

Area Constraints

In addition to thermal constraints, an implant size should ideally possess a small form factor. In order to fit a large number of recording amplifiers into a single implantable chip, it can be desirable to reduce the size of each active pixel to, for example 20-80 µm pitch. However, this may severely constrain the possible CMOS implementations that can be used for in-pixel analog processing. In particular, large value resistors may be unsuitable because such resistors (e.g. polysilicon resistors) tend to occupy significant layout space. The size of capacitors may also be constrained by the reduced pitch, which has implications for filter time constants and kTC noise.

II. In-Pixel Processing of Spike Train Data

There are many ways to analyze extracellular voltage recordings from the brain. In some embodiments of the present disclosure, the sensor may be used for the recording of extracellular action potential waveforms. It should be appreciated that other embodiments of the sensor disclosed herein can be modified or utilized with other recordings methods such as those that measure local field potentials "LFPs" or intracellular action potentials.

Action potentials, often called "spikes" can be analyzed using a number of techniques (e.g. principal component analysis (PCA), wavelet methods, amplitude discrimination, template-matching, and the like). In many cases, the purpose of this analysis is to identity distinct neurons within a larger population of neurons by the characteristics of their spiking activity. Voltage recordings from implanted electrodes can be collected as time-series data, and snippets of the data can be flagged to contain putative action potential events, as determined by one or more detection techniques (e.g. non-linear energy operator, threshold crossing, Teager energy operator, and the like). For every recorded time-series of voltage data that contains a putative action potential, the analysis methods described herein can be used to extract meaningful, descriptive features of that waveform for the purpose of classification.

The features extracted during this processing may correspond to simple characteristics such as spike amplitude or spike width, or they may correspond to vectors in a mathematical space that may not have a simple intuitive interpretation. The similarity of spike waveforms as defined by these quantitative parameters can lead to the inference of a discrete number of signal sources (i.e. cluster analysis). One use of this data is to determine the a posteriori probability of a given voltage waveform originated from each one of a number of hypothetical sources (neurons) within a larger total population. These sources are sometimes referred to as 'units' rather than neurons in order to signify their hypothetical/putative nature. In some cases, these probabilities can be used as an input for further systems-level analysis. In other cases, an intermediate classification step can be performed where the spike is either assigned a discrete origin (neuron/unit) or disqualified from further processing.

According to embodiments of the present disclosure, some of these spike-based analysis methods can be implemented in analog circuits because the underlying mathematics of the operation can be expressed as a transfer function that is realizable using a combination of active filters. In particular, this can apply to spectral decomposition methods which use a set of basis functions (e.g. principal components, wavelets) to transform signals into a set of time-variant scores. In these cases, combinations of active filters and summing amplifiers can be used to constitute impulse responses that approximate correlations or convolutions with predetermined basis functions. The disclosed embodiments can be capable of approximating these linear operations within a single pixel, and in certain embodiments the output of the circuit may correspond to principal component scores. However, because the present disclosure can also incorporate components with nonlinear transfer characteristics (e.g. rectification, absolute value, exponential behavior, etc.) and nonlinear summation, its representational space need not be limited to linear methods. Indeed, the circuit(s) according to various embodiments herein can be designed specifically to be amenable to training techniques such as backpropagation, and the circuit can therefore be tuned to match target outputs without explicit knowledge of the required transfer characteristics in each discrete component. In other words, the circuit(s) according to various embodiments herein can be trainable or trained in a way such that meaningful features and transforms of the data can emerge from the system-level transfer function of the circuit, without explicitly designing the transfer functions of each component.

By implementing the methods described herein in the analog domain, key features can be extracted from the spike signal so that the resulting representation requires much less total data to be digitized (compressive sensing). In this way, essential features of the signal can be extracted without the energy overhead associated with digitization of the raw data stream. For instance, by converting a signal into principal component scores, those scores can be sampled at a much slower time resolution than the original signal while preserving information at high frequencies.

Methods are disclosed herein for approximating principal component decomposition or other spectral decomposition methods using realizable CMOS architectures with low power and area consumption. This data transformation can allow for simultaneous data de-noising and compression at a single-pixel level for an energy and area cost that is lower than direct digitization (i.e. Nyquist sampling).

The circuit architecture disclosed herein may comprise or utilize feed-forward cascades of simple filters and operators combined with summing amplifiers to build up multiple transfer functions of arbitrary complexity. These circuits can effectively decompose incoming signals into continuous score estimates, which in the case of a linear system, can correspond to the coefficients produced by correlation or convolution operations between the signal and a set of basis waveforms. Chosen appropriately, these transfer functions can constitute an orthonormal basis set with which to efficiently represent an input stream of certain statistics. These scores can be sampled with relatively low bit-depth and low sampling rate, thus reducing the digitization cost within the readout array. Further, data transmission rates can be significantly lowered by utilizing event-triggered readout schemes that take advantage of the natural sparsity of spike events: for example, scores below a certain threshold are discarded and only suprathreshold values are transmitted from the device.

III. Circuit Architecture

Referring to FIG. 1, the pixel design disclosed herein can be comprised of four distinct stages: (1) Signal Conditioning, (2) Filtering, (3) Summation, and (4) Digitization and readout. One or more of the stages can be implemented in a processor on an analog circuit. In some embodiments, the processor can be implemented within a pixel on a chip. An array of sensors may be provided on a chip. The array may comprise a plurality of the pixels and the processors. In some embodiments, the pixel density in the array can be $\geq 2,500$ pixels/cm$^2$. In some cases, the pixel density in the array can be $\geq 15,000$ pixels/cm$^2$. In some embodiments, the array of sensors may comprise an array of CMOS sensors. Each sensor can be bonded to a passive electrode including an ECoG array, an array of microwires, an array of silicon probes, or an array of flexible electronic probes. The array can be part of an active silicon probe that is inserted into brain. Examples of microwires, microelectrodes, bundles of microwires, array of microwires or microelectrodes, and methods for fabricating the aforementioned are described in U.S. patent application Ser. No. 15/482,583 (published as US 2017/0290521) entitled "Neural-Interface Probe and Methods of Packaging the Same" which is incorporated herein by reference. Each sensor can be in direct contact with neurons or neural tissue via metallization, organic semiconductors, III-V semiconductors, IV semiconductors, or through a capacitive passivation film. The circuit architecture and signal processing methods described herein are also suitable for use with the system and methods for processing neural signals disclosed in PCT Patent Application PCT/US2017/048759 (published as WO/2018/039648) which is incorporated herein by reference.

Referring to FIG. 1, the (1) Signal Conditioning can present a large input impedance to the signal source and amplify the small neural signal with low noise. It may comprise band-pass filters to filter the incoming signal, by rejecting high and low frequency noise in bands where action potentials have little to no power. The conditioned signal may then be transformed through a (2) bank of linear and/or nonlinear filters and/or operators which may be subsequently (3) mixed in a weighted summation through a network of differential summing amplifiers to build a filter kernel that produces the desired output response. This network may be designed for maximal linearity in its summation or it may incorporate nonlinear transfer characteristics. Finally, the transformed signal (4) can be sampled, digitized and read out.

One of the features of the disclosed design is that it can accomplish spectral decomposition using a circuit topology similar to Artificial Neural Networks (ANN). ANN may be comprised of (in a typical configuration) data inputs connected to layers of interconnected multi-input single-output (MISO) nodes which themselves may comprise of an input-weighted summing junction fed through a linear or nonlinear activation function (e.g. linear, sigmoid function, tan h, softmax, etc.). With sufficient nodes, connectivity and choice of activation function, an ANN can be trained to approximate the output of arbitrary functions for given inputs by adjusting the weights of inputs of each summing junction. In analog electronics, a weighted summing amplifier circuit can be an accurate emulation of ANN nodes.

An important aspect of the present disclosure therefore is that the same circuit topology can be adjusted to perform spectral decomposition using different basis functions by changing the component values within the network. These weights can be theoretically or manually calculated to implement relatively simple, linear schemes. Alternatively, these weights can be "trained" using established techniques in machine learning and optimization theory such as back-propagation and gradient descent or more advanced optimizers (e.g. Levenberg-Marquardt, BFGS, Adam optimizer, etc.).

While an idealized analog circuit can exactly replicate the function of an ANN node, in practice, the real-world non-ideal behavior of amplifiers, parasitics, and the use of nonlinear diode-connected or source-follower transistors in place of resistors (as described below) adds in a nonlinear behavior that marks a departure from conventional ANN configurations. In traditional neural networks, summation typically occurs linearly and the nonlinear activation function is applied subsequently. In contrast, in the model disclosed herein, the weights of the summation step may themselves be voltage-dependent. This additional nonlinearity may be minimized by design in some embodiments to more closely resemble a linear system or ANN, but in other embodiments the nonlinearity may be harnessed or utilized to increase the richness of possible transfer functions that can be realized in the summing layer. In the latter case, the optimizer can determine on a component by component basis an extent by which nonlinearity increases or reduces total system error, and can adjust the component parameters accordingly.

With respect to the scope of the arbitrary nature of the approximated function, an example of a linear principal component decomposition is described herein. The function can be chosen to be another arbitrary continuous function that is realizable given the orthogonality and completeness of the input bank. The function(s) may include other feature extraction spectral decomposition methods (e.g. linear discriminant analysis, nonlinear kernel-based PCA and related methods, wavelet transformations, etc.); arbitrary transfer functions; posterior probabilities of class membership (logistic regression); or other probability density functions.

In summary, a structure (physical circuit topology) is disclosed herein that can perform spectral decomposition on voltage waveforms while minimizing implant size and energy dissipation. In a preferred embodiment, the voltage waveforms can correspond to neural extracellular recordings and action potential waveforms as described herein. Specific embodiments of the present disclosure can be realized by a discrete number of filters and summing amplifiers to be included in the network, as well as the parametric values chosen for each component within the circuit.

A. Stage 1 (Signal Conditioning)

In the preferred embodiment of neural recording, which is constrained by low power and low area requirements, the signal conditioning stage can have specifications as follows.

Minimization of total area and power.
Input referred RMS noise below 10 $\mu V_{rms}$.
Very high input impedance (>1 GΩ)
AC coupled to remove DC offset from electrode.
Two stage amplification: high bandwidth amplifier followed by low bandwidth one.
AC coupled on second stage to remove intrinsic input-offset from the first stage.

Figure 2:
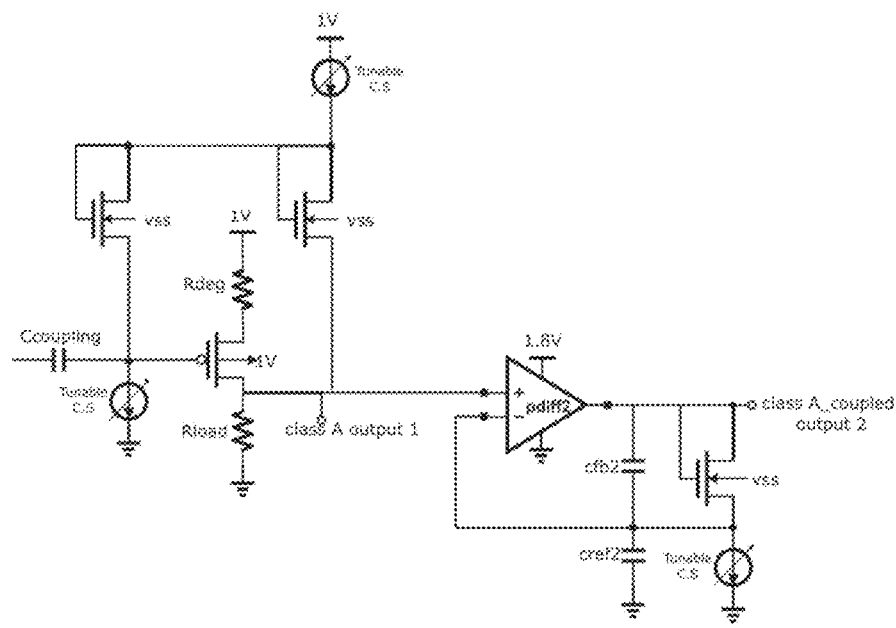
FIG. 2 illustrates a circuit diagram of a signal conditioning stage in accordance with some embodiments.

In an example embodiment of FIG. 2, the first amplification stage may include a Class A amplifier using a PMOS transistor. This design can minimize area and power consumption in the first stage. The second stage, in this example, may include an operational amplifier having a smaller bandwidth than the first amplifier which reduces input referred noise for the system.

Figure 3:
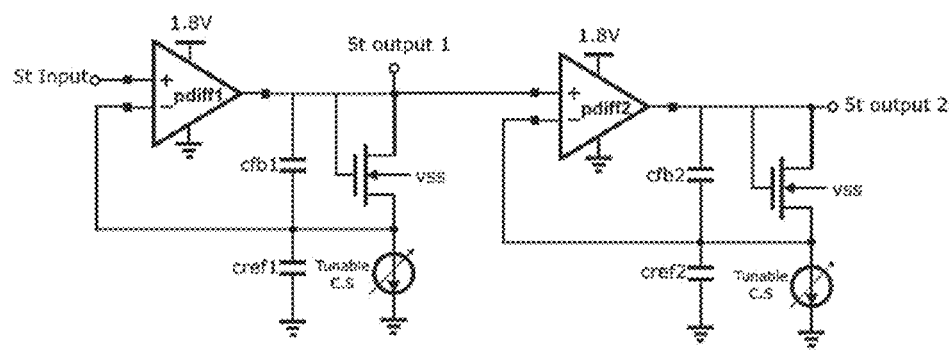
FIG. 3 illustrates a circuit diagram of a signal conditioning stage in accordance with some other embodiments.

Another embodiment is shown in FIG. 3. Here two operational amplifiers may be cascaded.

Figure 4:
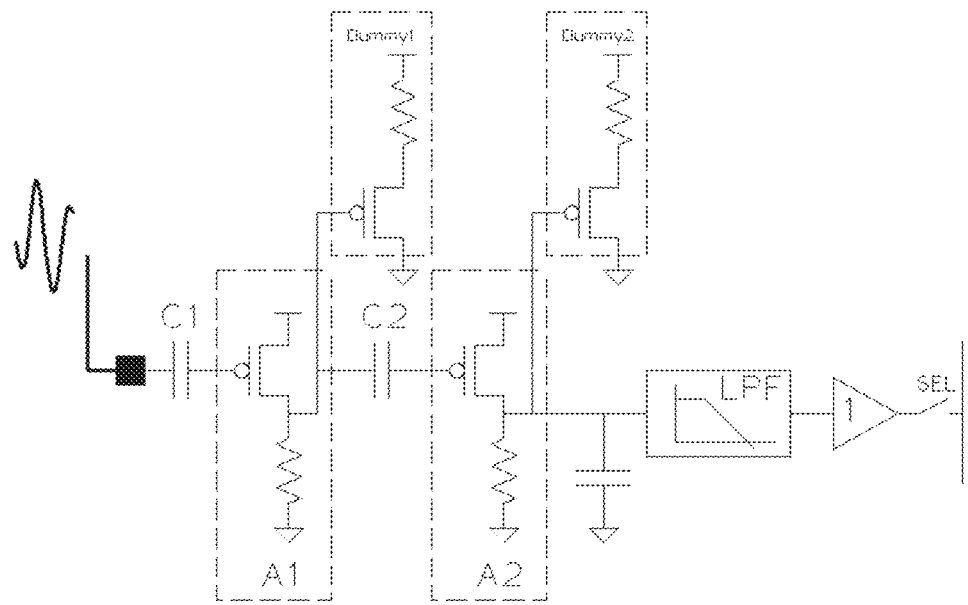
FIG. 4 illustrates a circuit diagram of a signal conditioning stage in accordance with some other embodiments.

In the preferred embodiment of FIG. 4, a low-noise amplifier that can reach 10 $\mu V_{rms}$ input referred noise, is shown. Realizing such low noise performance in a single stage amplifier would result in a circuit configuration with both a high power dissipation (beyond the allowed budget per pixel) and a high amplifier load capacitance (in the order of 50 pF).

In the preferred embodiment of FIG. 4, this issue is avoided by using a two-stage amplifier, whereby the first stage is not specifically designed to reach the noise specification on its own, yet has a much higher than required bandwidth. The second stage has a bandwidth matched to the required signal bandwidth and will cut out a section of the broadband noise power of the first stage. Such a topology can reach the noise specification, without requiring a huge capacitor.

In the preferred embodiment of FIG. 4, a two-stage amplifier configuration where each stage is a class A amplifier, made up of a PMOS transistor, is used.

AC coupling capacitors at the input of the first stage and in between the two stages avoid amplifier saturation under large DC gain.

In any of the embodiments (including that of FIG. 2, FIG. 3, and FIG. 4), the first coupling capacitor can be a large metal-insulator-metal (MIM) capacitor. Because MIM capacitors use space in the metallization layers and not in the silicon layer, a large capacitor (>1 pF) can be realized without substantially impacting the total pixel area.

Due to the nature of class A amplifier, the current into the amplifying transistor is modulated by the input signal which makes a signal-dependent current to flow from the power supply. In a large array of low-noise class A amplifiers driven from a common power rail (such as this invention), signal activity in one pixel causes the amplifiers in other pixels to experience an IR drop due to the signal-dependent power supply current and non-zero power supply metal interconnect resistance. Since a class A amplifier has a very low power supply rejection ratio, this phenomenon directly impacts the noise performance of the pixel and is therefore a serious issue in the case of a large array of low-noise class A amplifiers. In the preferred embodiment of FIG. 4, the signal-dependent power supply current fluctuations are suppressed by adding dummy branches which compensate for the current fluctuations in each amplifier.

Other embodiments using different circuit configurations for a voltage/current/charge amplifier with one or more stages may be implemented. Design features may include minimizing total capacitor area, replacing large value resistors with tunable diode-connected or source-follower transistors, reducing bandwidth after the first gain stage, minimizing the number of transistors in the first gain stage to maintain low noise, and implementing a large capacitor as a MIM capacitor so that it does not take up significant area in the silicon layer.

B. Stage 2 (Filtering)

The bank of filters and operators constitute a set of basis functions that can be combined in the subsequent processing stages to synthesize basis functions of greater complexity. Filter selection aims for 1) completeness—that any representative waveform signal can be approximated in low rank as a combination of one or more filter responses and 2) economy—that no greater number of filters are included in the bank than necessary (i.e. over-complete representation). It is not necessarily the case that the individual filters themselves need to provide orthogonal basis for signal decomposition since orthogonality, if desired, can be achieved in the subsequent processing stages, but in general filters with highly correlated output may not lead to economical circuits.

Different filters can be configured to extract different temporal features of the signal waveforms. Such filters may occupy low area and draw low power while designed to have as close to an ideal response as possible.

Figure 5:
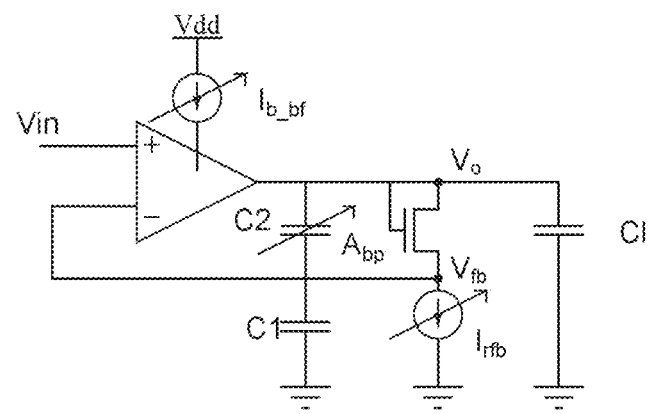
FIG. 5 illustrates an example of a first order low-pass, high-pass, and band-pass filter.
Figure 6:
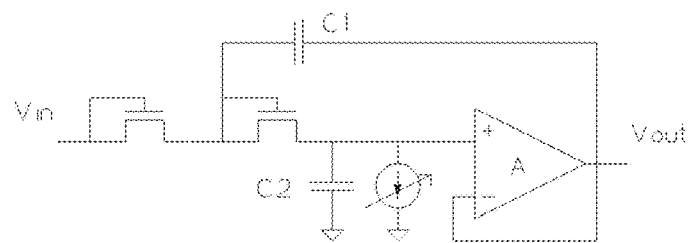
FIG. 6 illustrates an example of a second order low-pass filter.
Figure 7:
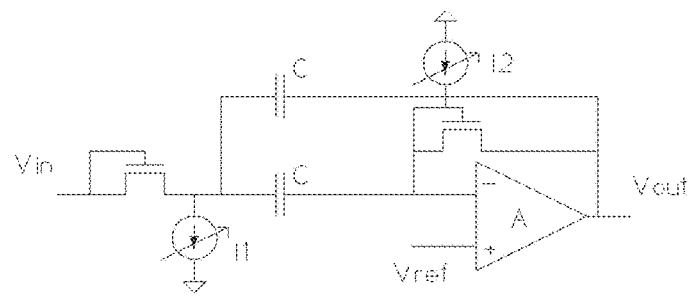
FIG. 7 illustrates an example of a second order resonant band-pass filter.
Figure 8:
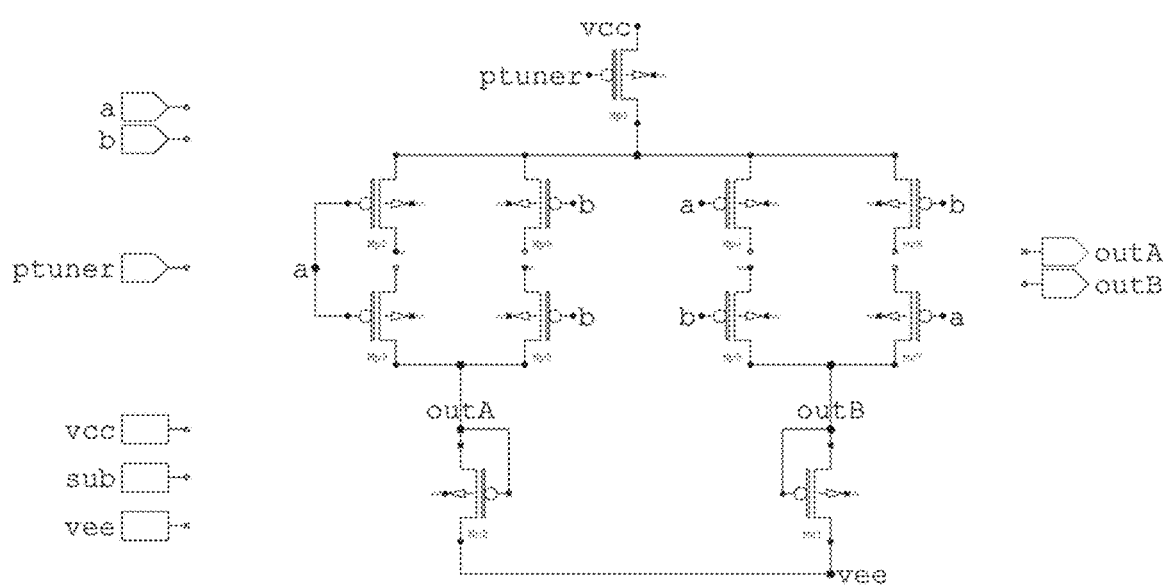
FIG. 8 illustrates an example of an absolute value operator.
Figure 11:
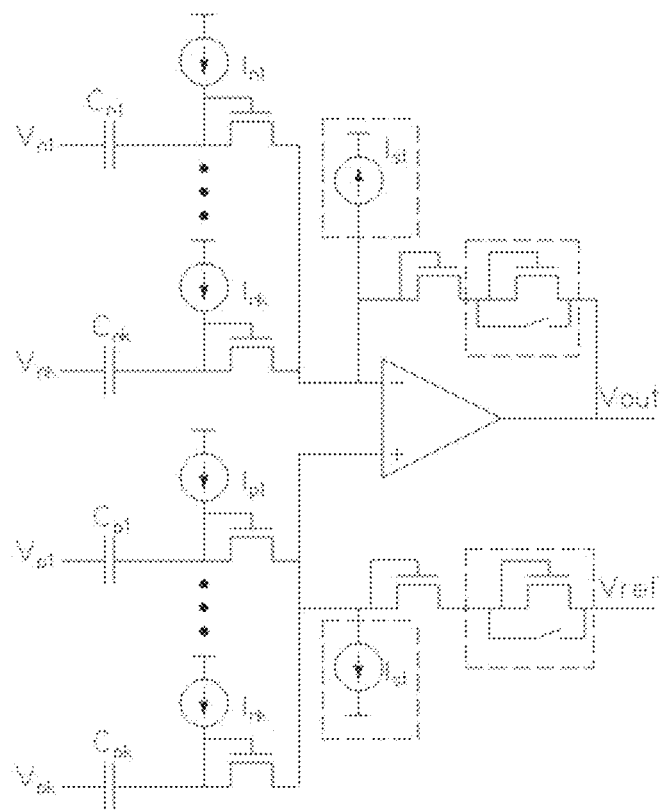
FIG. 11 shows a summing amplifier with positive and negative input weights set by diode-connected transistors, in accordance with some embodiments.
Figure 12:
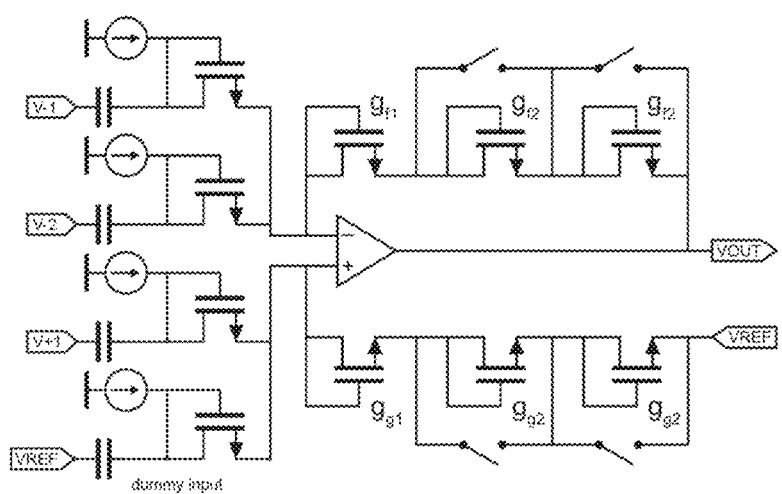
FIG. 12 shows a summing amplifier with positive and negative input weights set by diode-connected transistors, in accordance with some embodiments.

Different circuit topologies can be used to implement the filters of the input bank. Some embodiments may include, for example: a first order low-pass, high-pass, or band-pass filter (FIG. 5), a second order low-pass filter (FIG. 6), a second order resonant band-pass filter (FIG. 7), an absolute value operator (FIG. 8), and the like. A feature of the circuits disclosed herein is that large value resistors can be replaced with diode-connected or source-follower transistors, thus allowing for a large range of corner frequencies with a limited area budget.

Each of the filter circuits disclosed herein can be tuned using current mirrors and thus the filters can be optimized post-production to account for deviations from simulation.

It should be appreciated that similar active filters can be constructed with high-pass, band-pass, low-pass, resonant, band-stop, notch or all-pass characteristics.

The filter bank can also include other nonlinear operators such as "logarithmic function" or "exponential function" or the signal raised to arbitrary powers or the signal multiplied with another signal using analog multiplier. Signals can be rectified using a half-wave rectifier to allow only positive or negative signals to pass through.

Additionally or optionally, an untransformed signal can be passed directly to the summing layer as one of its inputs. In the preferred embodiment, a pixel may comprise 4-16 different filters or operators.

Within the filter bank, chains of filters may be concatenated in series. In the case of filter circuits, this may lead to higher order filters. Allowing for combinations of filters and nonlinear operators can lead to more elaborate transfer characteristics.

C. Stage 3 (Summation)

As described herein, transfer functions of higher complexity can be achieved by putting a diversity of simple filters and/or operators in series, but complexity can also be achieved by summing the outputs of multiple filters using a summing junction, which can act as an analog mixer circuit.

In one embodiment, the summing weights and connections between the filter bank and summation layer can be optimized computationally (in silico) to minimize reconstruction error of the output of a set of summing amplifiers versus the desired target output (e.g. PCA scores) or to maximize discriminability of different spike classes. To make the circuit trainable, physical parameters in the circuit can be linked to trainable weight parameters.

Some examples of summing topologies with positive and negative input weights that can be implemented in the summation stage are shown in FIGS. 9A, 9B, 9C, 9D, 10, 11, 12, 13, and 14.

A feature of this summing layer is that the summing amplifiers can use diode-connected or source-follower transistors to approximate resistors with orders of magnitude difference in resistance values. In contrast, if the summing amplifier were realized using traditional polysilicon resistors, it could occupy orders of magnitude more area. Further, these transistors-as-resistors can open new possibilities for computation within the network, since their properties can be tuned.

Figure 13:
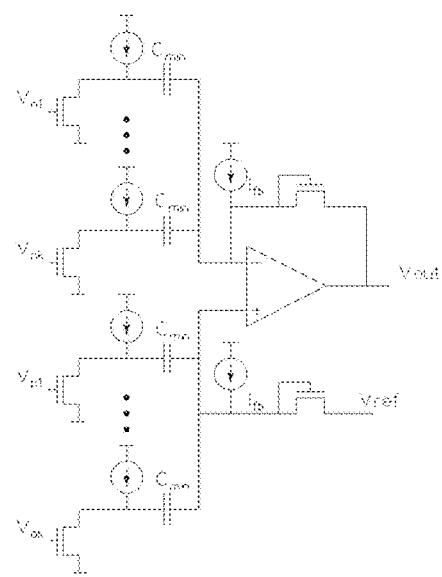
FIG. 13 shows a summing amplifier with positive and negative input weights set by source follower transistors, in accordance with some embodiments.

One preferred embodiment is shown in FIG. 13. Here the impedance in the input branches are implemented as source follower transistors which enable programming of the resistor values by changing the bias currents thus allowing for different summing weights to be programmed. The capacitors in the input branches block the DC bias current while still allow the signal (AC) current to be summed by the operational amplifier.

Figure 14:
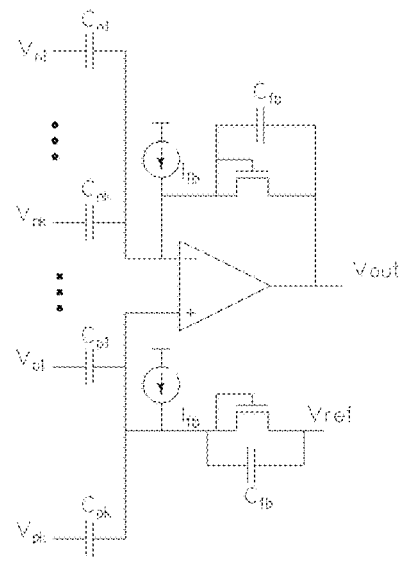
FIG. 14 shows a summing amplifier with positive and negative input weights set by capacitor values, in accordance with some embodiments.

A second preferred embodiment is shown in FIG. 14. Here the impedance in the input branches and the feedback branch are implemented as capacitors. This embodiment provides a better linear summing operation than the first embodiment, at the expense of programmability of the summing weights.

In an embodiment where nonlinearities are minimized, the summing layer may comprise building up detailed and elaborate impulse responses by the superposition of many simpler convolution kernels from the filter bank. When the operational amplifiers in the summing layer are tuned to have nonlinear voltage transfer characteristics (e.g. sigmoid function, tan h, softmax, etc.), then the network of summing junctions may become a traditional cascade feed-forward artificial neural network (ANN). As such, the network can be trained by, e.g. gradient descent and backpropagation. Finally, when the diode-connected or source-follower transistors that approximate the weights (resistors) of the summing junction are themselves operating under conditions of nonlinearity, the circuit can be trained to perform nonlinear transformations.

The outputs of the filter bank can connect fully or partially to a number of summing amplifiers. Each summing amplifier may be a Single Input Single Output (SISO), Single Input Multiple Output (SIMO), Multiple Input Single Output (MISO) or Multiple Input Multiple Output (MIMO) component. Summing amplifier inputs can connect to either the inverting or non-inverting terminals of the operational amplifier to allow for positive or negative weights in the summation. Outputs of summing amplifiers may themselves fully or partially connect to other summing amplifiers or to the (4) Digitization and Readout stage, in a cascade or standard feedforward or recurrent network structure.

To incorporate nonlinear activation functions in analogy to ANN, the amplifier properties may be tuned for maximum linearity or may be designed for highly nonlinear voltage transfer characteristics in order to more closely mimic, for example, the sigmoidal activation function commonly used in artificial neural networks (ANN).

In each summing junction, the contribution of each branch may be a weighted sum of its voltage, weighted through an impedance or admittance function of the input branches and feedback branch.

In certain embodiments, the final analog output layer may be assumed to be a summing amplifier, but it is also possible to apply subsequent filters and/or operators after summing amplifiers layer prior to digitization.

D. Stage 4 (Event Detection and Sampling)

The traditional approach for pixel array readout may be to sample analog values from each pixel and multiplex them onto the output drivers. Such a scheme may have certain undesirable design features, for example: (1) large power dissipation due to the need of transmitting analog signals along the readout lines with high fidelity, or (2) the need for implementing on-chip analog to digital converters (ADC) which consume a lot of power.

Embodiments of the present disclosure described herein can include alternative readout schemes for which a combination of any of the following features may apply, including event-based readout, sparse readout, digitization of pixel level data, reduction of frame rate, dynamic event thresholding, noise estimation, synchronous and asynchronous sampling, timestamps, and XY coordinates of the pixel.

Event-based sparse readout can apply to the analog values, or to the digitized values. The sparse readout can be event driven and described as follows. When a pixel (sensor array element) senses an "event", the pixel may send a signal out, which can be for example, a binary signal in X- and/or Y-direction to the in-chip peripheral circuits to notify that an event occurred in that row and/or column. The circuit can be equipped for readout of the detailed information at a later stage. Thereby data mass is reduced as only pertinent information is read out and pixels without pertinent information remain silent and untouched.

Chunks or slices of the array information may be copied to a processing area that is on the same IC, but outside the array area. In an alternative embodiment/configuration, the processing area may be on a separate IC that is connected to the pixel array via, for example a 3D-integration technique using wafer bonding, through-silicon-vias (TSV's), and the like, but not limited thereto. The processing area can be equipped to perform data reduction and/or multiplexing of the copied information before readout.

The pixel level data (e.g. analog information, analog values, voltages, currents, times or charge quantities) can be digitized on-chip (e.g. in-pixel, or in the periphery of the pixel array). Digitization can include, for example: converting to a digital number, as in an ADC; converting to a pulse width, where the length of the pulses is a measure for the analog value, in a "amplitude to time" circuit of which an example is shown further; or converting to a series of ONEs or ZEROs where the number of consecutive ONEs or ZEROs is a measure for the analog value.

The frame rate (frequency at which each pixel in the array is sampled, or accessed) can be reduced below the time resolution needed to accurately track the input signals to the pixels by storing the information of an event in the pixel, together with a "timestamp".

The timestamp can be, for example: (1) a digital number representing the time at which the sample was taken; (2) an analog value representing the time i.e., an analog voltage proportional to the number of milliseconds elapsed after an external event (e.g., applied pulse or transition); or (3) an analog value that is a measure of the time elapsed between the time the sample was taken and the time the sampled value is finally readout from the pixel.

A combination of the above approaches can simultaneously reduce the volume of data that is transmitted from the sensor array and can also eliminate the need for digitization of the full signal by on-chip or off-chip ADCs, thus reducing the power consumption.

In a preferred embodiment, upon detection of an 'event', a sensor can sample the outputs of 3 summing amplifiers representing the first three transformed principal component scores. These values can then be digitized, along with the XY coordinate and timestamp of event occurrence within the current frame.

Embodiments of the present disclosure include the following power-saving features: (1) The outputs of the summing amplifiers can be digitized at a substantially lower sampling rate and bit-depth than would otherwise be required to transmit the raw data. (2) The readout of the circuit can be event-driven, meaning that the outputs are digitized and transmitted only if a putative action potential is detected.

In the following, the continuous analog output of a summing amplifier may be occasionally referred to as a "score" in keeping with the terminology of principal component analysis (i.e. PC scores), but the word "score" as used herein may mean 'output value'.

Each of the summing amplifiers may continuously output scores based on the input signal, but these values may only be meaningful whenever an action potential is occurring or has recently occurred. Further, in many schemes the output scores may be most meaningful at a particular point in time, as defined by the training, and continuously sampling them throughout for example the course of an action potential may not yield additional information.

To conserve energy and bandwidth, it is therefore desirable to "gate" the readout of the summing amplifiers, i.e., sampling the value at the correct moment in time and not otherwise. The conditions for gating will be discussed subsequently.

Figures 15A, 15B:
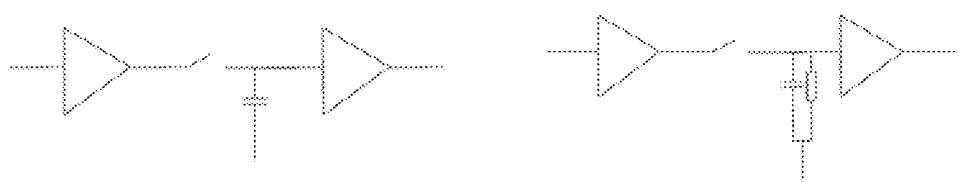
FIG. 15A illustrates an example of a standard sample-and-hold circuit.
FIG. 15B illustrates a sample-and-hold circuit with resistor load in parallel to the capacitor, in accordance with some embodiments.

In one embodiment, control over sampling can be achieved by using a standard sample-and-hold circuit shown in FIG. 15A. By introducing a leak current (by a resistor, a resistor-like device, a "switched capacitor" emulation of a resistor, a current source, or the like) in parallel to the sample and hold capacitor, a circuit can be implemented that samples an instantaneous value and then decays to reference potential. For example, FIG. 15B shows a sample-and-hold circuit with resistor load in parallel to the capacitor. The output of the circuit can accomplish amplitude-to-time conversion that allows for a subsequent comparator to digitize the sampled value, resulting in a binary waveform that codes the analog information in the width of a pulse.

Figure 16:
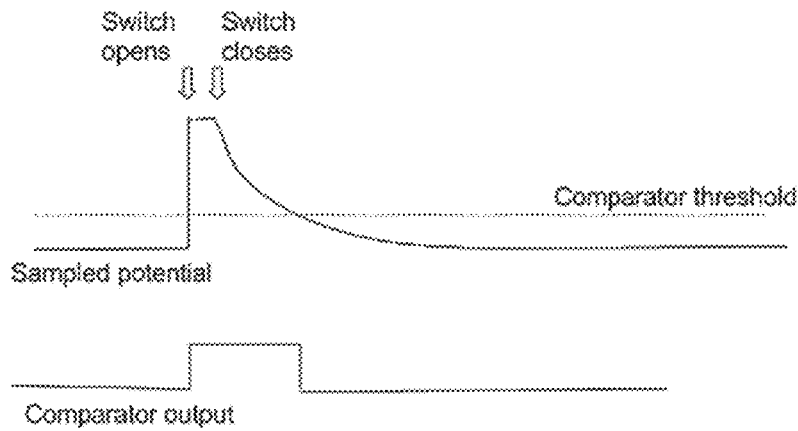
FIG. 16 illustrates the discharging of a capacitor though a load resistor.
Figure 17:
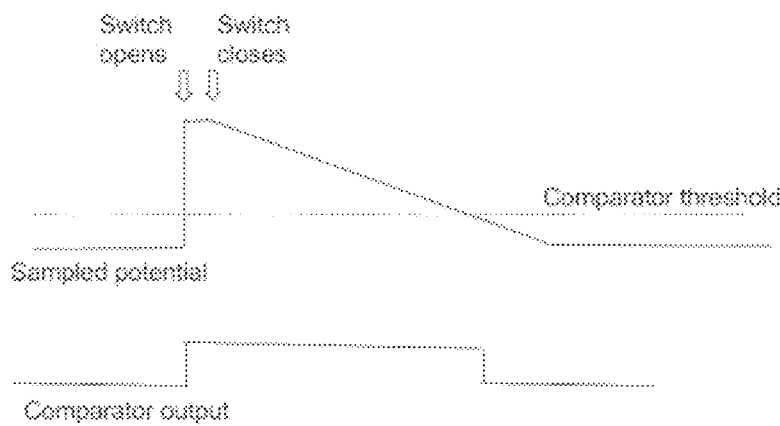
FIG. 17 illustrates the principle of analog-to-pulse width conversion by discharging a capacitor though a constant current source.

FIG. 16 shows a simplified diagram for a signal that has only positive values. By using two such circuits with diodes of opposite polarity, a signal that has both positive and negative excursions can be digitized. Alternatively, an absolute value operation can be performed on the signal to only require diodes of single polarity. For sake of simplicity, a resistor was used in the above example. In some embodiments, in order to hold the discharge rate constant, a current source can be used, resulting in a more linear amplitude-to-pulse width conversion, if such is desired. For example, FIG. 17 shows analog to pulse width conversion with current source.

Figures 18A, 18B:
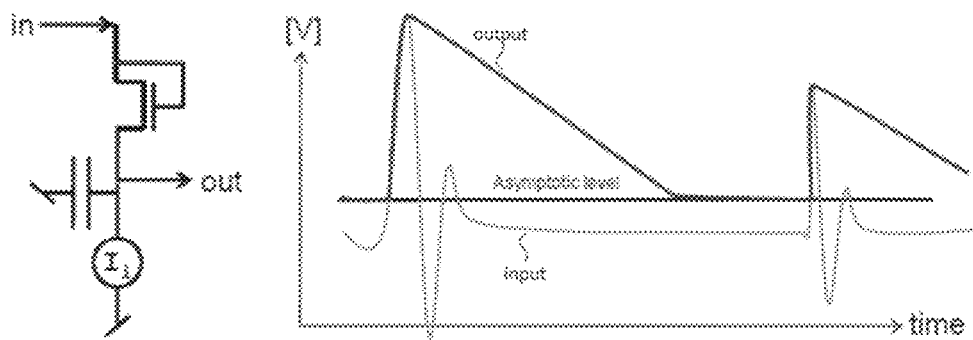
FIG. 18A illustrates an exemplary circuit realizing (analog pulse height) to (analog pulse width) conversion, in accordance with some embodiments.
FIG. 18B illustrates the expected waveforms at the input and output of FIG. 18A.

In another embodiment, a diode-connected or source-follower transistor and current source can be used to encode the peak amplitude during the period while the sampling occurs. For example, FIG. 18A shows an exemplary circuit embodiment realizing (analog pulse height) to (analog pulse width) conversion. FIG. 18B shows the expected waveforms at the input and output. The output shown here can be fed into a comparator to result in the final binary pulse.

The arrangement of FIGS. 18A and 18B can be advantageous over others because the circuit can be trained to output scores in response to action potential waveforms—where the maximally informative value is a time-local extremum—then the precise timing of the sampling is not critical as long as the peak is contained within the sampling window.

There are two general approaches to sampling the outputs of the summing amplifiers: (1) synchronous sampling and (2) asynchronous sampling.

In a synchronous sampling scheme, one or more of the summing amplifiers may be continuously monitored by a comparator against a threshold that may be fixed or may itself be a function of the input signal. For instance, one summing amplifier may encode the first principal component, and when the score exceeds a fixed threshold, the comparator output goes (logically) HIGH and all of the summing amplifiers may be sampled at that same instant.

This sampling can be accomplished when the transition HIGH from the comparator output causes the sampling switch to close, and the "hold" capacitor is charged to the value of the summing amplifier output. The sampling switch may include, for example a MOS transistor operated as an analog switch with the comparator output connected to its gate, as described previously.

In some cases, rather than opening throughout the entire duration of the gating pulse signal, the switch may open only transiently on the rising edge of the pulse from the comparator. In this case, it responds to the first derivative of the comparator output, which can be achieved using a simple RC circuit. This can lead to a shorter sampling period and higher temporal precision.

The temporal precision of a sampling circuit is normally shorter than the width of the sample pulse. The circuit "tracks" the input signal as long as the sampling switch in "on" ("closed"), and memorizes the last tracked value on opening (equivalent to turning off) the switch.

In embodiments involving more than one comparator to detect whether or not an event has occurred, the HIGH and LOW outputs of the comparators can be combined with logical operators (e.g. AND, OR, NOT, XOR and other derived logical functions) that determine whether or not sampling and transmission of the summing amplifier outputs should occur.

Sampling criteria can combine analog processing and digital logic. For instance, the output of a summing amplifier may be monitored for the precise time at which a peak occurs (derivative=0) "AND" the magnitude of the signal is greater than 'n' times a reference value.

Figure 19:
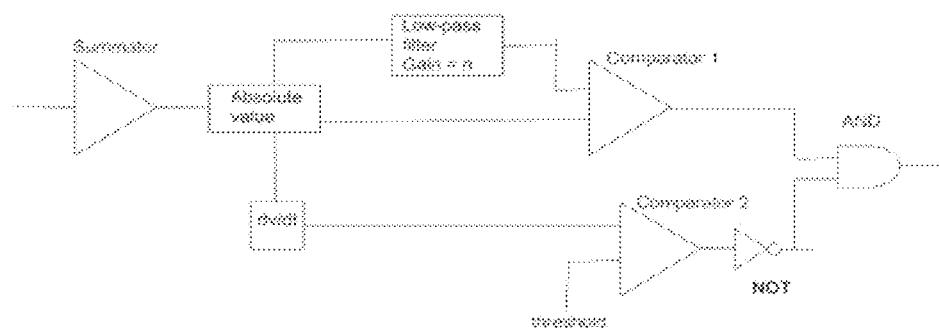
FIG. 19 illustrates a block diagram of a circuit to trigger readout of summing amplifiers, in accordance with some embodiments.

This reference value can be a fixed value or a function of the signal itself, e.g. $V_{rms}$. FIG. 19 shows a block diagram of an exemplary circuit to trigger readout of summing amplifiers. It should be appreciated that many possible logical conditions may be applied to determine the sampling moment for the summing amplifier outputs in a synchronous configuration.

It is further noted that the "derivative" function dv/dt shown in FIG. 19 is in fact an analog domain filter, resembling the "high-pass filter". The circuit can be implemented with other temporal analog filters (e.g. high-pass, low-pass, band-pass, all-pass, resonant, finite impulse response, and the like as known to persons skilled in the art).

A characteristic of the synchronous readout scheme is that it requires precise sampling and at least one of the summing amplifiers to produce a precisely timed signal on which to trigger sampling for all output summing amplifiers for all possible spikes.

An event detection and sampling circuit may be of multiple input—multiple output (MIMO) configuration where at least one input is a master input and at least one other input is a slave input. For each input, a storage capacitor can be provided to store the value of the input.

Figure 20:
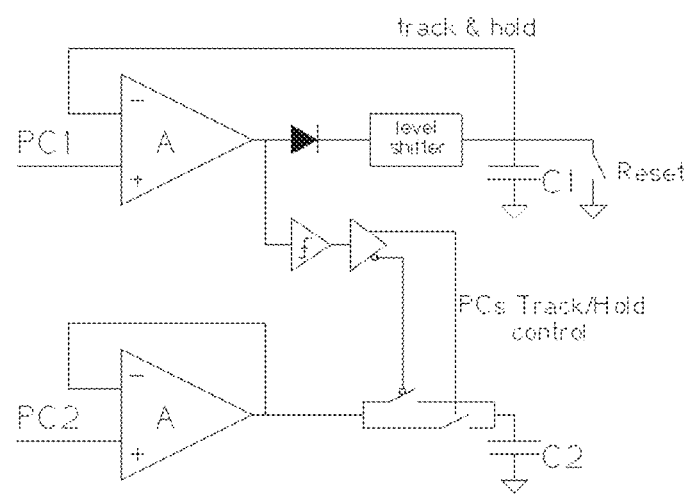
FIG. 20 illustrates a peak track and hold circuit in accordance with some embodiments.

In some embodiments, at least one of the capacitors is part of a track-and-hold circuit that stores an extreme value of a master input, described herein as "peak track-and hold circuit". A preferred embodiment of such a circuit is shown in FIG. 20.

The peak tracking and hold circuit may function to store any one or more of the following: the maximum value of the master input; the minimum value of the master input; the maximum value of the absolute value of the master input. For simplicity, the following description relates to tracking the maximum value, but those skilled in the art will appreciate that the embodiments can also be used to track the minimum value.

The peak track-and-hold circuit continuously compares its input to the value stored on its capacitor. So long as the input is not lower than the stored value, the stored value will track the input. This regime of operation is described herein as "tracking mode".

Conversely, if the input becomes lower than the stored value, the stored value will cease to track the input and will not change. This regime of operation is described herein as "holding mode".

In the preferred embodiment of FIG. 20, at least one of the capacitors is part of a "slave" track-and-hold circuit where it is gated by a signal originating from the "master" peak track-and hold circuit.

When the master circuit is in tracking mode, it signals to one or more slave circuits to also track their input signals. Conversely, when the master circuit is in holding mode, it signals to the one or more slave circuits to also hold their inputs. This timing relationship is shown in FIG. 28.

It should be appreciated that outputs from multiple peak track-and-hold circuits can be combined using logical operators. For example, in some embodiments, the gating signal to a slave circuit may originate from a combination of a master and one or more than one slave track-and-hold circuits.

Figure 28:
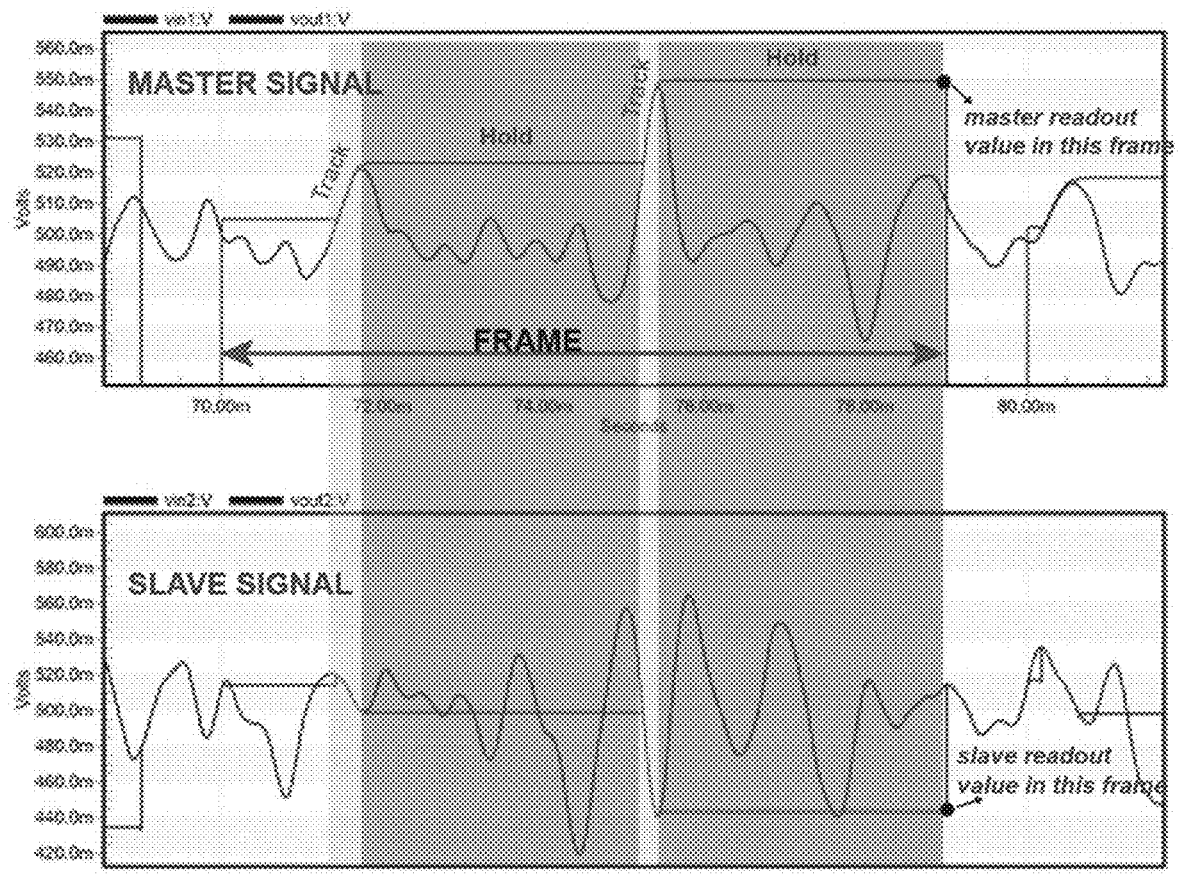
FIG. 28 illustrates in-phase synchronization of a slave signal to a master signal in accordance with some embodiments.

In a preferred embodiment of FIG. 20, one master circuit is responsible for gating all of the slave circuit(s) so that their track and hold periods are synchronized and in phase with the master as shown in FIG. 28.

Figure 21:
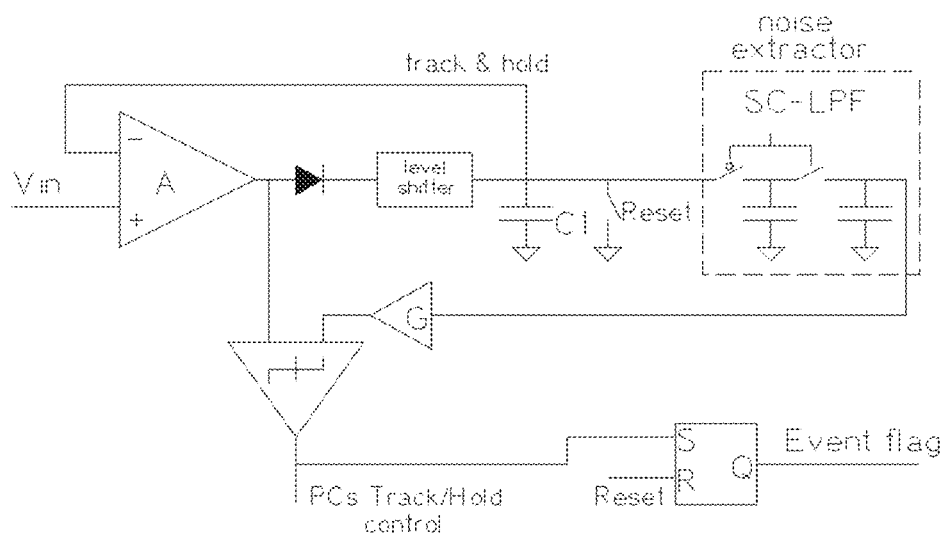
FIG. 21 illustrates a readout threshold triggering circuit in accordance with some embodiments.

The stored values held on the master and slave capacitors can be read out in a threshold-triggered manner with the help of circuit shown in FIG. 21. Periodically, the stored value on the master capacitor is compared to a threshold. If the master stored value exceeds the threshold, an event flag is raised and latched on to a digital or analog storage element, to be picked up later by the sparse readout switch matrix in the sensor array. The master stored value is then transmitted to one of the event detection and sampling circuit output channels, and at the same time the values of one or more slave capacitors are also transmitted on their respective output channels.

Upon threshold triggering and subsequent transmission of the master and slave capacitor values, the capacitors are reset to some baseline value that is below the threshold value. In some embodiments, the reset action can also be performed periodically (fixed or arbitrary intervals).

The threshold of readout triggering may be a fixed value. Alternatively, the threshold may be a dynamic value that approximates or is proportional to a filtered version of the master or input signal. This may be an approximation of the noise on that channel. Noise may mean RMS noise, peak-to-peak noise, or any other definition of noise known to those skilled in the art.

Figure 22:
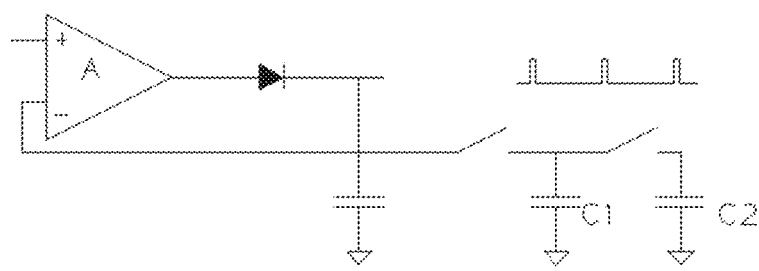
FIG. 22 illustrates a noise estimation circuit in accordance with some embodiments.
Figure 29:
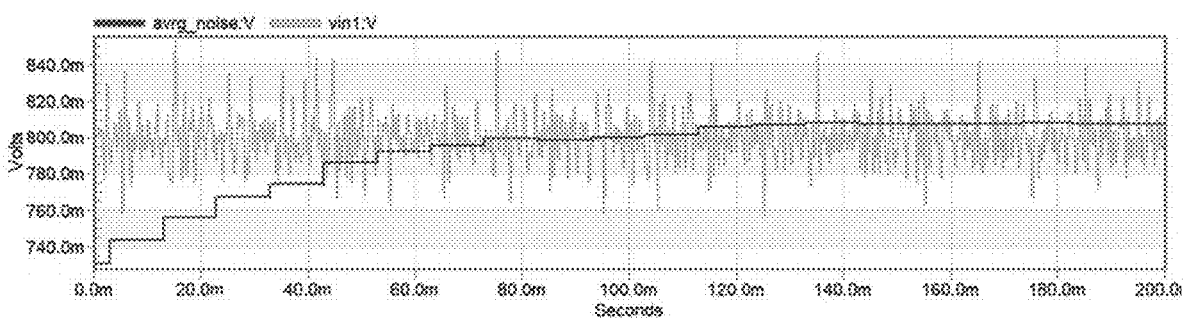
FIG. 29 illustrates in-phase synchronization of a slave signal to a master signal in accordance with some embodiments.

In the preferred embodiment, the threshold of triggering is set as arbitrarily proportional to the noise floor of the master output channel. This is achieved by averaging the peaks in the master signal by means of a peak tracking circuit followed by a switched-capacitor or continuous time low-pass filter as shown in FIG. 22. The output of this circuit builds up a signal over time that is proportional to RMS noise in its input signal, for example as shown in FIG. 29.

This signal may then be scaled up or down by an amplifier and/or a level-shifter to construct a threshold value that is arbitrarily proportional to the signal's noise floor. Alternatively, the threshold may be scaled by amplifying the threshold signal prior to filtration.

This dynamic thresholding circuit is superior to the fixed thresholding scheme because it adapts the threshold of readout triggering based on the spatial and/or temporal changes in the noise floor of sensor elements in the array.

Sparse readout of the array is performed at periodic intervals called "frames". The peak track-and-hold circuit also stores intra-period timing (e.g. timestamps) of the last held peak value which is then readout along with the master and signal values stored on the capacitors. Such a scheme can be realized by a capacitor storing a fixed initial value at the beginning of the frame that is subsequently discharged by a constant current. The longer the elapsed time, the lower the voltage over the capacitor.

All the analog values read out of the sensor array (including master and slave signals and timestamps) can be subsequently digitized using on chip ADCs before off-chip transmission. ADCs may be of the traditional type known to people skilled in the art but may also be based on comparators, pulse-width encoders or time-to-digital converters. Alternatively, analog values out of the array can also be transmitted for off-chip digitization.

Figure 23:
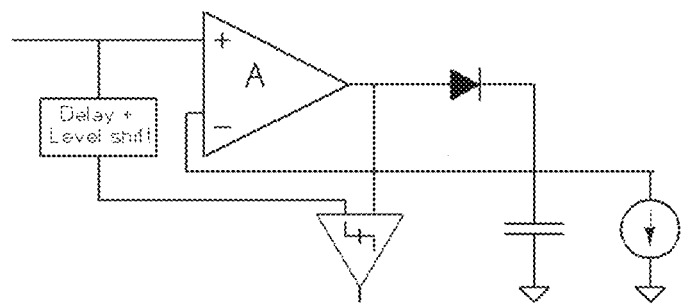
FIG. 23 illustrates an asynchronous peak detector circuit in accordance with some embodiments.

Event detection and readout triggering can also be performed asynchronously by using a peak detector circuit. An embodiment of peak detector circuit is shown in FIG. 23. In this case, the summing amplifiers may directly connect to the peak detector and the circuit can be trained so that each summing amplifier produces transients spikes in response to action potential signals where the spike height encodes the component score. In this case, the peaks of the summing amplifiers need not be simultaneous. Each summing amplifier can trigger its own readout each time it is HIGH. The sampling moments of the different summing amplifiers may thus differ in time, even depending on the actual signal contents.

A characteristic of the asynchronous encoder may be that some summing amplifiers may produce scores with a lower signal to noise ratio than others. It may therefore be undesirable to have noisy channels triggering their own readout. A hybrid embodiment is one where noisy channels may be gated by low noise channels, but the sampling window may be of a similar time course to that of an action potential waveform, i.e. between 1 and 10 ms. In this case, the use of a peak detector can allow for asynchronous sampling, but the gating of noisy channels may ensure that they will not transmit data other than periods when bona fide action potentials are occurring.

Because the final output of the circuit will include digital HIGH and LOW signals, the sensor described here can be adapted to event triggered readout by a switch matrix.

IV. Large Value Programmable Resistors in Low-Area CMOS

Implementing large value resistors in CMOS technology in the limited chip area can be difficult. The sheet resistance of polysilicon is not very high (~400Ω/□ in 180 nm technology node) compared to the materials available in making discrete resistors. At this level, implementing a 1 GΩ resistor in serpentine form factor may require an area of ~400 μm×400 μm. This may not be feasible especially when several high-value resistors need to be replicated in an array of thousands of pixels.

Figure 24:
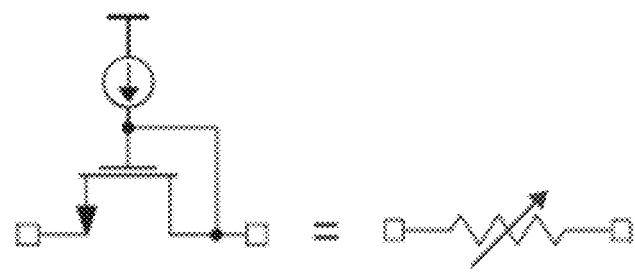
FIG. 24 illustrates an example of a diode-connected transistor.
Figure 25A:
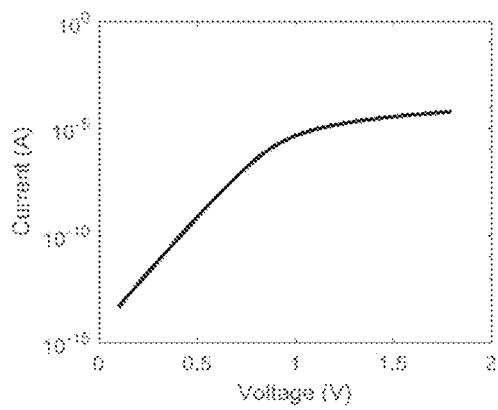
FIGS. 25A and 25B illustrate the current-voltage relationship and incremental resistance of the transistor of FIG. 24.
Figure 25B:
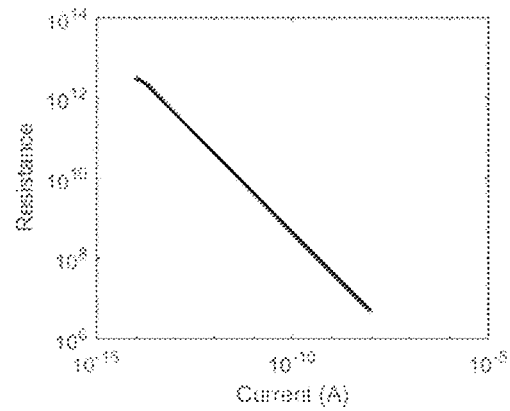

To achieve such high resistances in standard CMOS process technology, a MOSFET can be utilized in shorted gate-drain configuration, called "diode-connected transistor", as shown in FIG. 24. The transistor can be biased in subthreshold operation mode where the incremental (small-signal) resistance (dv/di) is given by $r_{ds} \approx nV_T/I_{bias}$, where n is a device constant, $V_T$ is the thermal voltage (25 mV at room temperature), and $I_{bias}$ is the bias current. Extremely high resistance values (GΩ-TΩ range) can readily be achieved by biasing the transistor in nA to sub-pA regime, as shown in FIGS. 25A and 25B.

This diode-connected transistor scheme can offer multiple benefits towards the implementation of tunable filters, trainable weighted summing amplifiers, and other tunable electronic circuits. Advantages include the ability to realize large resistance values in a small footprint and compatibility with standard CMOS technology without the need for extra processing steps. In terms of trainability of the weighted summing amplifiers, a large dynamic range of weights (5-6 orders of magnitude) can be made available by changing the bias current of the diode-connected transistor. The tunability of diode-connected transistors also allows for adjusting the time constants, corner frequencies, and Q-factors of the filters and other analog circuits which rely on a resistor values or current source values as design parameters. Furthermore, by changing the bias current through a programmable current mirror, the weight of the summing branches can be tuned even after the CMOS chip is fabricated. This can offer increased flexibility and robustness against manufacturing variations and provides a means towards neuromorphic ANN implementation.

The incremental resistance of a diode-connected transistor is highly nonlinear. Therefore, where linear I-V characteristics are required, the signal swing across the transistor can be limited to small-signal regime (<5 mV).

Limiting the signal swing across the diode-connected transistors can be one way of maintaining linearity in the circuit response. However, even when the weights themselves have some nonlinear characteristics, a linear approximation can still be achieved at a network level by careful tuning of the relative weights and by tuning the voltage transfer characteristics of the summing amplifiers.

Additionally, in other embodiments, the nonlinearity of the I-V curve in the transistors that establish the weights can be harnessed. For instance, when inputs to the summing amplifiers are much larger (>>5 mV) than the small signal regime, the summing amplifier can constitute a nonlinear sum which also allows for training the circuit with nonlinear characteristics (e.g., exaggerating the contribution of larger inputs).

Figure 26:
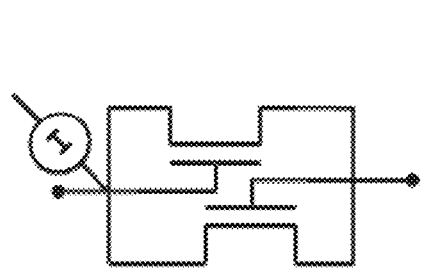
FIG. 26 illustrates an example of two antiparallel diode-connected transistors.
Figure 26:
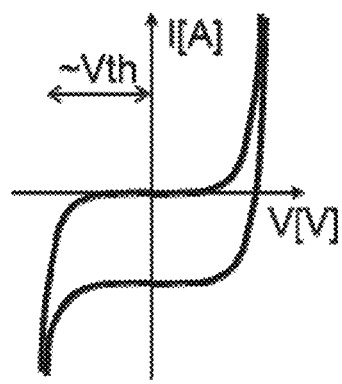

The above-described concept of a diode-connected transistor can also be extend to an arrangement comprising two antiparallel diode-connected transistors (FIG. 26).

Figure 27:
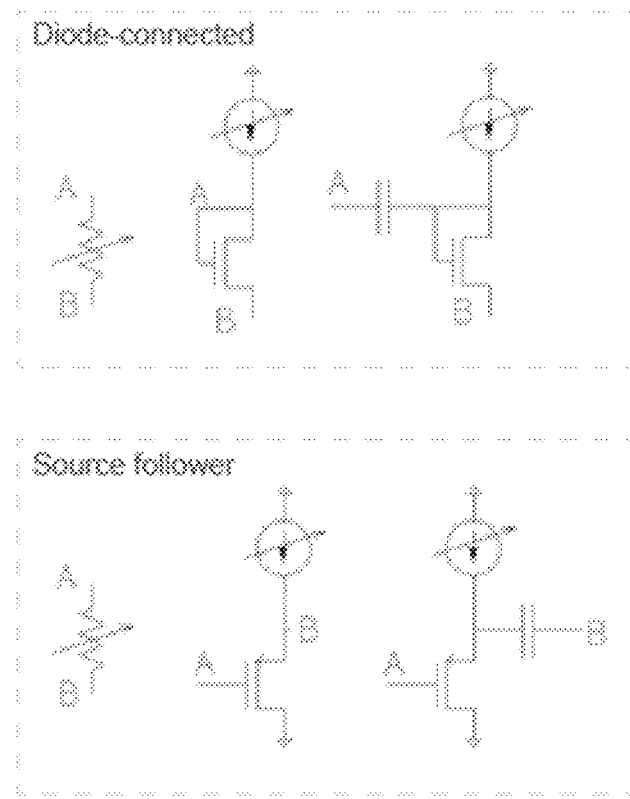
FIG. 27 illustrates diode-connected transistor and source follower transistor configuration to approximate large value resistors with and without DC blocking.

Another method of approximating large resistors in CMOS technology is to use the source-follower configuration of the MOSFET as shown in FIG. 27. In this topology, the incremental (small-signal or AC) resistance (dv/di) is also given by $r_{ds}=1/gm=nV_T/I_{bias}$.

All above-described embodiments may be combined with series capacitors to achieve DC blocking of the bias current, as shown in FIG. 27, thus allowing for independent programming of the small signal resistance of two or more transistors connected in parallel, series or in any combination.

V. Component Selection and Parameter Tuning

In some embodiments, the circuit may be trained to reproduce correlation or convolution coefficients with basis functions, e.g. principal component scores for a set of defined training inputs.

This can be achieved by approximating a transfer function that transforms the signal input into output principal component scores. To synthesize this transfer function, it is informative to start by estimating a transfer function $H(s) = N(s)/D(s)$ using numerical regression so that the numerator ($N(s)$) and the denominator ($D(s)$) approximate $Y(s) = H(s) X(s)$ with the fewest number of 'z' zeros and 'p' poles within reasonable accuracy (where $Y(s)$ is the desired output and $X(s)$ is the input data in the Laplace domain).

Having obtained an approximation of the transfer function, $H(s)$, this can be expanded or approximated into a sum/product of lower order transfer functions using partial fraction expansion or another approximating technique. This approach makes it possible to synthesize arbitrary transfer functions from a collection of lower-order analog filters that are realizable in integrated circuit design. Thereof, if the resulting series of transfer functions have poles and zeros which are sufficiently stable and physically realizable in an analog circuit, they can be used as some of the initial configurations of filters in the filter bank used in this invention. For example, if one expanded transfer function is simply $1/s$, this could be implemented as an integrating low-pass filter in an analog circuit.

The preceding method may be used to design the filter bank and summation circuit. It can be used to determine component selection and filter network topology, and to initialize values for the component parameters. The resulting circuit can be subsequently optimized using machine learning techniques (described later) to account for non-ideal behavior of the circuits (e.g. parasitic capacitances, nonlinearity).

The filters and summation weights need not be rationally selected via the above. They can alternatively be designed arbitrarily, with components being arbitrarily selected from a set of components, and circuit topology parameters (i.e. number of circuit layers, number of components per layer) also being randomly selected. Component parameters can also be initialized stochastically. In this case, circuit performance may be determined wholly by optimization.

Optimization can be accomplished, for instance, using a hierarchical model that simulates different circuit components or subcircuits in a circuit simulation program (e.g. SPICE), where the input-output relationship for each component model can be established, and where the change in output can be calculated with respect to any of the device model parameters (for a given input). Numerical differentiation of the input-output function for each component with respect to each tunable parameter and input means that backpropagation (chain rule) can be applied to find the change in system outputs with respect to each parameter.

In some embodiments, the sensor can be designed such that the output(s) of the analog circuit can consist of undefined/abstract bases set which are a result of applying machine learning techniques to the circuit training. For example, during training, the output(s) of the analog circuit can be fed into or stacked with the input(s) of an ANN (e.g., logistical classifier, autoencoder, etc.) and the entire model can be trained to produce the desired target ANN outputs. For instance, the network may be trained so that the ANN output reproduces class identity for labeled datasets, or the same model can be trained to reproduce posterior probabilities for class membership. In that case, the outputs of the circuit may represent an intermediate representation of the neural data that is to be decoded by the same ANN used in training. Alternatively, the information-rich outputs of the analog circuit can be used for subsequent processing without the accompanying ANN.

In a similar embodiment, the combined circuit and ANN can be trained so that the ANN outputs produce a reconstruction of the original input to the circuit. It may also output a denoised version of the original input. In this case, the circuit output may represent the dimensionally limiting layer of an autoencoder, or de-noising autoencoder, respectively.

By building a hierarchical model of the circuit described above and elsewhere herein, and combining it with a traditional ANN in simulation, it is possible to train the entire system using machine learning techniques.

In some embodiments, the digitized circuit outputs can be used as inputs to the ANN in simulation. In other embodiments, the outputs of the summing amplifier layer can be used for training to a particular set of targets, and the digitization layer can be added subsequent to that initial training.

In some embodiments of the training, regularization terms (e.g. L1, L2 norms) can be added to the training objective function that further optimizes circuit parameters such as silicon area and power.

Training the circuit together with an ANN to readout its values is a powerful training method: it can generate compressive encoding schemes that satisfy an end requirement (the ANN target) without constraining the analog circuit to output the desired target directly. This allows for some of the computation to be moved outside of the silicon. Indeed, by applying stringent regularization terms to the silicon portion of the system while leaving the ANN unconstrained, it is possible to build circuits with minimal power and area requirements that still transmit essential feature information.

Simulation of the entire circuit using e.g. SPICE is also possible, and optimization of the entire circuit can be done either in an iterative fashion or by running many parallel models and selecting candidate designs for further optimization, or a combination of both.

Methods for local gradient-based optimization as well as global optimization methods including Hessian methods, genetic methods, particle swarm, etc. or gradient-free training (e.g. genetic algorithms) can be used.

In cases where asynchronous readout is desired, the sensor can be trained to produce output(s) whose peak amplitude(s) encode pertinent information, and do not transmit anything when the output(s) do not exceed a threshold value.

Finally, an advantage of this design is that the diode-connected or source-follower transistors can be adjusted by tunable current sources. This means that small differences in performance between simulation and fabrication can be adjusted/calibrated after production of the silicon. These adjustments in the actual silicon can themselves be guided using optimization techniques.

A neural data processor is disclosed herein. The neural data processor can comprise an analog circuit configured to process an input neural signal that is collected with aid of a sensing device. The analog circuit can comprise (1) at least two filters configured to transform the neural signal, and (2) at least one summing element configured to sum transformed outputs of the at least two filters, to process the neural signal and thereby extract a plurality of features from the neural signal.

In some embodiments, the sensing device may comprise at least one microelectrode, and the neural signal comprises an extracellular electrical recording collected using the at least one microelectrode. In some cases, the sensing device may comprise an optical sensor, and the neural signal may comprise a change in light intensity.

In some embodiments, the at least one summing element may comprise a plurality of summing elements. In some embodiments, (1) the filters can be configured having a set of predefined complex poles and zeros, and (2) the plurality of summing elements can be configured having a set of predefined summing weights, such that outputs of the plurality of summing elements convey temporal features of the neural signal. In some cases, the analog circuit can be configured to extract the plurality of features based on an a priori feature set derived from previously recorded and/or modeled neural activity. The a priori feature set can be encoded in the filters and the at least one summing element.

In some embodiments, the plurality of filters and the plurality of summing elements can be implemented as cascading layers in the analog circuit. In some instances, the plurality of summing elements may comprise linear summing circuits. Additionally or optionally, the plurality of summing elements may comprise nonlinear summing circuits. In some cases, the nonlinear summing circuits may comprise an artificial neuron.

In some embodiments, the plurality of filters and the plurality of summing elements can be collectively used to encode one or more linear transfer functions. Alternatively, the plurality of filters and the plurality of summing elements can be collectively used to encode one or more nonlinear transfer functions. The one or more transfer functions may approximate a correlation or convolution operation(s) of the neural signal with a linear basis set, and decomposition of the neural signal may be based on the linear basis set. In some cases, the basis set may be selected based on analysis of prior neural signal data. Alternatively, the basis set need not be selected based on an explicit statistical prior. In some embodiments, the basis set may be approximated by linear summations and/or cascades of one or more filter transfer functions. The linear summations and/or cascades of the one or more filter transfer functions may be implemented as active filter circuits and summing amplifiers. In some cases, the basis set may be chosen from an arbitrary set of basis functions including wavelets. In some embodiments, the output of one or more summing amplifiers can be further acted upon by additional filters and/or operators. In some embodiments, tunable transistors can be used in place of resistors within the analog circuit.

In some embodiments, the analog circuit may comprise a plurality of stages comprising of (1) a first stage, (2) a second stage, and (3) a third stage, wherein the filters are implemented in the second stage, and the summing elements are implemented in the third stage. In some cases, the first stage may comprise a low-noise amplifier and signal conditioning circuit configured to amplify and condition the neural signal before it is provided to the plurality of filters in the second stage. In some cases, the second stage may further comprise one or more nonlinear operators. The filters can be programmable for adaptation to a plurality of different types of feature extraction. The summing elements can be programmable to provide different types of summing behavior. The filters can be optimized for linear behavior, low power dissipation, and/or a reduced circuit area or footprint. In some embodiments, the predefined weights of the summing element can be optimized for linear behavior, dynamic range of weights, power dissipation, and/or a reduced circuit area or footprint.

In some embodiments, the analog circuit can be configured to provide one or more outputs to an event detection and sampling circuit. In some cases, the event detection and sampling circuit can be provided on a same chip as the analog circuit. In some cases, the event detection and sampling circuit is not a peripheral device to the analog circuit. In some cases, the processor may further comprise the event detection and sampling circuit. The processor can be implemented within a pixel on the chip. In some embodiments, an array of sensors may be provided on the chip. The array may comprise a plurality of the pixels and the processors. In some cases, the pixel density in the array can be $\geq 2{,}500$ pixels/cm$^2$. In some cases, the pixel density in the array can be $\geq 15{,}000$ pixels/cm$^2$. In some embodiments, the array of sensors may comprise an array of CMOS sensors. In some embodiments, the pixels or a subset of pixels in the array may comprise circuitry to extract local field potentials (LFPs) of the neural signal. In some embodiments, each sensor may be bonded to a passive electrode including an ECoG array, an array of microwires, an array of silicon probes, or an array of flexible electronic probes. In some cases, the array may be part of an active silicon probe that is inserted into brain. In some embodiments, each sensor can be in direct contact with neurons or neural tissue via metallization, organic semiconductors, III-V semiconductors, IV semiconductors, or through a capacitive passivation film. In some embodiments, the analog circuit described above is also capable of processing non-neural transient signals including optical, seismic, radar, or ultrasound.

In some embodiments, the outputs of the analog circuit may collectively constitute a low rank approximation of a neural signaling event when sampled at a specific point in time during or after the neural signaling event. The event detection and sampling circuit can be configured to transmit values of all of the outputs from the analog circuit when one or more triggering conditions are met.

In some embodiments, the event detection and sampling circuit can be configured to transmit the values at a time instance only when the one or more triggering conditions are met. In some cases, the event detection and sampling circuit does not transmit any values when the one or more triggering conditions are not met, so as to reduce an overall data transmission rate of the system.

In some embodiments, the one or more outputs from the analog circuit may comprise a master output and one or more slave outputs. The one or more triggering conditions may comprise a peak value of the master output exceeding a threshold. In some instances, the peak value of the master output may be transmitted and recorded only when the peak value exceeds the threshold. Instantaneous values of the one or more slave outputs can be synchronously transmitted and recorded at the moment the master output reaches a peak, whenever that peak value exceeds a threshold. In some embodiments, the threshold can be dynamically derived from the master output or the neural signal. In some cases, the dynamic threshold can be proportional to the root mean square value of the master output or the neural signal. In some cases, the threshold is a fixed value. In some cases, the threshold can be a value that is programmed externally and input to said processor. The event detection and sampling circuit can be configured to transmit the values from the analog circuit for digitization.

VI. Extensions of the Present Disclosure Beyond Neuroscience

A sensor circuit and method of training the circuit have been described herein. This sensor circuit can be optimized for processing time-variant signals with the following characteristics:

Signal of interest is composed of transient events
The events are sparse in time
Events have temporal features that follow a known statistical distribution
Signal power spectrum lies within a frequency range of 5 Hz-500,000 Hz For signals falling into the above category, the disclosed circuit is capable of compressively sensing on a per event basis, and its discrete output, which is only triggered in the case when events occur, lends itself to sparse readout methods. This means that large-format arrays can be constructed containing thousands to millions of these sensors, and industry-standard sparse readout methods can be employed to achieve further efficiency of data transmission. Thus massively parallel compressive sensing arrays can be constructed to convey event statistics from thousands to millions of signal sources.

Embodiments of the present disclosure are useful in situations where power constraints dictate that the full analog readout of a large sensor array or in-pixel digitization is difficult to realize or where the combined speed and array size results in an impractical number of outputs given other circuit constraints.

Embodiments of the present disclosure can also be used to process other signals that are not sparse, where its ability to decompose the signals (in real time) into scores for a set of basis functions is valued without the compressive step of sparse readout.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments described herein may be employed. It is intended that the following claims define the scope of the disclosure, and that methods and systems within the scope of these claims and their equivalents be covered thereby.

What is claimed is:

1. A neural data processing system, comprising:
a sensing device configured to collect a neural signal,
a neural data processor comprising an analog circuit configured to process the neural signal, thereby obtaining a processed neural signal,
wherein the analog circuit comprises (1) at least two filters configured to transform the neural signal, and (2) a plurality of summing elements configured to sum transformed outputs of the at least two filters to generate a plurality of transfer functions, thereby extracting a plurality of features from the neural signal,
wherein the plurality of transfer functions approximate a correlation or convolution operation(s) of the neural signal with a linear basis set approximated by linear summations and/or cascades of the plurality of transfer functions, and wherein decomposition of the neural signal is based on the linear basis set; and
a brain-machine interface (BMI) configured to transmit the processed neural signal to an external device.

2. The processing system of claim 1, wherein the analog circuit comprises a plurality of stages comprising of (1) a first stage, (2) a second stage, and (3) a third stage, wherein the at least two filters are implemented in the second stage, and wherein the plurality of summing elements are implemented in the third stage.

3. The processing system of claim 2, wherein the first stage comprises a low-noise amplifier and signal conditioning circuit configured to amplify and condition the neural signal before the neural signal is provided to the at least two filters in the second stage.

4. The processing system of claim 2, wherein the second stage further comprises one or more nonlinear operators.

5. The processing system of claim 2, wherein the at least two filters are programmable for adaptation to a plurality of different types of feature extraction.

6. The processing system of claim 2, wherein the plurality of summing elements are programmable to provide different types of summing behavior.

7. The processing system of claim 1, wherein the analog circuit is configured to extract the plurality of features based on an a priori feature set derived from previously recorded and/or modeled neural activity.

8. The processing system of claim 7, wherein the a priori feature set is encoded in the at least two filters and the plurality of summing elements.

9. The processing system of claim 1, wherein at least one summing element of the plurality of summing elements comprises one or more nonlinear summing circuits.

10. The processing system of claim 9, wherein the one or more nonlinear summing circuits comprises an artificial neuron.

11. The processing system of claim 1, wherein the basis set is chosen from an arbitrary set of basis functions including wavelets.

12. The processing system of claim 11, wherein the basis set is not selected based on an explicit statistical prior.

13. The processing system of claim 1, wherein the sensing device comprises at least one microelectrode, and wherein the neural signal comprises an extracellular electrical recording collected using the at least one microelectrode.

14. The processing system of claim 1, wherein the sensing device comprises an optical sensor, and wherein the neural signal comprises a change in light intensity.

15. The processing system of claim 1, wherein (1) the at least two filters are configured having a set of predefined complex poles and zeros, and (2) the plurality of summing elements are configured having a set of predefined summing weights, such that outputs of the plurality of summing elements convey temporal features of the neural signal, and wherein the plurality of features comprises the temporal features.

16. The processing system of claim 1, wherein the at least two filters and the plurality of summing elements are implemented as cascading layers in the analog circuit.

17. The processing system of claim 1, wherein at least one summing element of the plurality of summing elements comprises one or more linear summing circuits.

18. The processing system of claim 1, wherein the basis set is selected based on analysis of prior neural signal data.

19. The processing system of claim 1, wherein the linear summations and/or cascades of the plurality of transfer functions are implemented as active filter circuits and summing amplifiers.

20. The processing system of claim 1, wherein the sensing device is configured to be implanted in a subject's brain.

21. The processing system of claim 1, wherein the external device is located outside of a subject's brain from which the neural signal is collected.

22. The processing system of claim 1, wherein the BMI operably couples the sensing device and the neural data processor.

23. The processing system of claim 1, wherein the processed neural signal is wirelessly transmitted to the external device.

24. The processing system of claim 1, wherein the BMI comprises the neural data processor.

* * * * *